(12) United States Patent
Baxter, III et al.

(10) Patent No.: US 8,353,438 B2
(45) Date of Patent: *Jan. 15, 2013

(54) CIRCULAR STAPLER INTRODUCER WITH RIGID CAP ASSEMBLY CONFIGURED FOR EASY REMOVAL

(75) Inventors: Chester O. Baxter, III, Loveland, OH (US); John V. Hunt, Cincinnati, OH (US); Danius P. Silkaitis, Mason, OH (US); Jeffrey P. Wiley, Milford, OH (US); Paul T. Franer, Cincinnati, OH (US); John B. Schulte, West Chester, OH (US); Daniel J. Abbott, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 245 days.

This patent is subject to a terminal disclaimer.

(21) Appl. No.: 12/621,679

(22) Filed: Nov. 19, 2009

(65) Prior Publication Data

US 2011/0114698 A1    May 19, 2011

(51) Int. Cl.
*A61B 17/115* (2006.01)
*A61B 1/313* (2006.01)
(52) U.S. Cl. .............. 227/176.1; 227/175.1; 606/1
(58) Field of Classification Search ..... 227/175.1–182.1, 227/19
See application file for complete search history.

(56) References Cited

U.S. PATENT DOCUMENTS

| | | | |
|---|---|---|---|
| 2,853,074 A | 9/1958 | Olson | |
| 3,359,978 A * | 12/1967 | Smith, Jr. | 604/161 |
| 3,490,675 A | 1/1970 | Green et al. | |
| 3,551,987 A | 1/1971 | Wilkinson | |
| 3,643,851 A | 2/1972 | Green et al. | |
| 3,662,939 A | 5/1972 | Bryan | |
| 3,717,294 A | 2/1973 | Green | |
| 3,819,100 A | 6/1974 | Noiles et al. | |
| RE28,932 E | 8/1976 | Noiles et al. | |
| 4,331,277 A | 5/1982 | Green | |
| 4,383,634 A | 5/1983 | Green | |
| 4,396,139 A | 8/1983 | Hall et al. | |
| 4,402,445 A | 9/1983 | Green | |
| 4,408,692 A | 10/1983 | Sigel et al. | |

(Continued)

FOREIGN PATENT DOCUMENTS

CA        2458946 A1    3/2003

(Continued)

OTHER PUBLICATIONS

U.S. Appl. No. 12/408,905, filed Mar. 23, 2009.

(Continued)

*Primary Examiner* — Lindsay Low

(57) ABSTRACT

Introducers for introducing a surgical circular stapler into a patient. Various embodiments comprise a hollow flexible sheath that has a distal end and an open proximal end that is sized to receive a stapling head portion of the circular stapler therein. A rigid cap assembly may be attached to the distal end of the hollow flexible sheath The rigid cap assembly may be configured to selectively move between a closed position wherein a distal face of the stapling head is covered and an open position wherein the distal face of the stapling head is exposed. A portion of the rigid cap assembly has a shape that substantially matches a perimetrical shape of a portion of the stapling head to enable the rigid cap assembly to pass proximally over the stapling head when the introducer is withdrawn from the patient.

20 Claims, 19 Drawing Sheets

U.S. PATENT DOCUMENTS

| | | |
|---|---|---|
| 4,415,112 A | 11/1983 | Green |
| 4,417,890 A * | 11/1983 | Dennehey et al. ............ 604/256 |
| 4,429,695 A | 2/1984 | Green |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,506,671 A | 3/1985 | Green |
| 4,522,327 A | 6/1985 | Korthoff et al. |
| 4,530,453 A | 7/1985 | Green |
| 4,566,620 A | 1/1986 | Green et al. |
| 4,573,622 A | 3/1986 | Green et al. |
| 4,580,712 A | 4/1986 | Green |
| 4,610,383 A | 9/1986 | Rothfuss et al. |
| 4,619,262 A | 10/1986 | Taylor |
| 4,629,107 A | 12/1986 | Fedotov et al. |
| 4,632,290 A | 12/1986 | Green et al. |
| 4,655,222 A | 4/1987 | Florez et al. |
| 4,664,305 A | 5/1987 | Blake, III et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,844,068 A | 7/1989 | Arata et al. |
| 4,869,414 A | 9/1989 | Green et al. |
| 4,869,415 A | 9/1989 | Fox |
| 4,921,479 A | 5/1990 | Grayzel |
| 4,941,623 A | 7/1990 | Pruitt |
| 4,944,443 A | 7/1990 | Oddsen et al. |
| 4,973,302 A | 11/1990 | Armour et al. |
| 5,065,929 A | 11/1991 | Schulze et al. |
| 5,071,430 A | 12/1991 | de Salis et al. |
| 5,074,454 A | 12/1991 | Peters |
| 5,104,025 A | 4/1992 | Main et al. |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,158,567 A | 10/1992 | Green |
| 5,205,459 A | 4/1993 | Brinkerhoff et al. |
| 5,211,649 A | 5/1993 | Kohler et al. |
| 5,221,036 A | 6/1993 | Takase |
| 5,222,963 A | 6/1993 | Brinkerhoff et al. |
| 5,222,975 A | 6/1993 | Crainich |
| 5,234,447 A | 8/1993 | Kaster et al. |
| 5,236,440 A | 8/1993 | Hlavacek |
| 5,239,981 A | 8/1993 | Anapliotis |
| 5,258,009 A | 11/1993 | Conners |
| 5,263,937 A | 11/1993 | Shipp |
| 5,282,806 A | 2/1994 | Haber et al. |
| 5,282,829 A | 2/1994 | Hermes |
| 5,285,945 A | 2/1994 | Brinkerhoff et al. |
| 5,304,204 A | 4/1994 | Bregen |
| 5,309,927 A | 5/1994 | Welch |
| 5,336,232 A | 8/1994 | Green et al. |
| 5,342,395 A | 8/1994 | Jarrett et al. |
| 5,342,396 A | 8/1994 | Cook |
| 5,350,400 A | 9/1994 | Esposito et al. |
| 5,366,479 A | 11/1994 | McGarry et al. |
| 5,397,324 A | 3/1995 | Carroll et al. |
| 5,404,870 A * | 4/1995 | Brinkerhoff et al. ......... 600/184 |
| 5,405,072 A | 4/1995 | Zlock et al. |
| 5,411,508 A | 5/1995 | Bessler et al. |
| 5,413,272 A | 5/1995 | Green et al. |
| 5,417,361 A | 5/1995 | Williamson, IV |
| 5,419,766 A * | 5/1995 | Chang et al. .................. 604/110 |
| 5,425,745 A | 6/1995 | Green et al. |
| 5,445,644 A | 8/1995 | Pietrafitta et al. |
| 5,452,837 A | 9/1995 | Williamson, IV et al. |
| 5,474,566 A | 12/1995 | Alesi et al. |
| 5,478,354 A | 12/1995 | Tovey et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,503,320 A | 4/1996 | Webster et al. |
| 5,503,635 A | 4/1996 | Sauer et al. |
| 5,505,363 A | 4/1996 | Green et al. |
| 5,507,426 A | 4/1996 | Young et al. |
| 5,509,596 A | 4/1996 | Green et al. |
| 5,520,700 A | 5/1996 | Beyar et al. |
| 5,529,235 A | 6/1996 | Boiarski et al. |
| 5,533,661 A | 7/1996 | Main et al. |
| 5,535,934 A | 7/1996 | Boiarski et al. |
| 5,540,375 A | 7/1996 | Bolanos et al. |
| 5,542,594 A | 8/1996 | McKean et al. |
| 5,553,765 A | 9/1996 | Knodel et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,575,799 A | 11/1996 | Bolanos et al. |
| 5,575,803 A | 11/1996 | Cooper et al. |
| 5,577,654 A | 11/1996 | Bishop |
| 5,580,067 A | 12/1996 | Hamblin et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,601,224 A | 2/1997 | Bishop et al. |
| 5,603,443 A | 2/1997 | Clark et al. |
| 5,605,273 A | 2/1997 | Hamblin et al. |
| 5,607,094 A | 3/1997 | Clark et al. |
| 5,607,095 A | 3/1997 | Smith et al. |
| 5,609,285 A | 3/1997 | Grant et al. |
| 5,620,452 A | 4/1997 | Yoon |
| 5,624,452 A | 4/1997 | Yates |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,780 A | 6/1997 | Green et al. |
| 5,639,008 A | 6/1997 | Gallagher et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,517 A | 9/1997 | Hooven |
| 5,667,527 A | 9/1997 | Cook |
| 5,669,544 A | 9/1997 | Schulze et al. |
| 5,669,918 A | 9/1997 | Balazs et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,685,474 A | 11/1997 | Seeber |
| 5,690,269 A | 11/1997 | Bolanos et al. |
| 5,692,668 A | 12/1997 | Schulze et al. |
| 5,695,504 A | 12/1997 | Gifford, III et al. |
| 5,697,543 A | 12/1997 | Burdorff |
| 5,697,943 A | 12/1997 | Sauer et al. |
| 5,702,408 A | 12/1997 | Wales et al. |
| 5,702,409 A | 12/1997 | Rayburn et al. |

| | | | |
|---|---|---|---|
| 5,704,534 A | 1/1998 | Huitema et al. | |
| 5,711,472 A | 1/1998 | Bryan | |
| 5,713,505 A | 2/1998 | Huitema | |
| 5,715,987 A | 2/1998 | Kelley et al. | |
| 5,716,366 A | 2/1998 | Yates | |
| 5,718,360 A | 2/1998 | Green et al. | |
| 5,725,536 A | 3/1998 | Oberlin et al. | |
| 5,725,554 A | 3/1998 | Simon et al. | |
| 5,730,758 A | 3/1998 | Allgeyer | |
| 5,732,871 A | 3/1998 | Clark et al. | |
| 5,732,872 A | 3/1998 | Bolduc et al. | |
| 5,743,456 A | 4/1998 | Jones et al. | |
| 5,752,644 A | 5/1998 | Bolanos et al. | |
| 5,752,965 A | 5/1998 | Francis et al. | |
| 5,752,970 A * | 5/1998 | Yoon | 606/185 |
| 5,758,814 A | 6/1998 | Gallagher et al. | |
| 5,762,256 A | 6/1998 | Mastri et al. | |
| 5,766,188 A | 6/1998 | Igaki | |
| 5,769,892 A | 6/1998 | Kingwell | |
| 5,779,130 A | 7/1998 | Alesi et al. | |
| 5,779,131 A | 7/1998 | Knodel et al. | |
| 5,779,132 A | 7/1998 | Knodel et al. | |
| 5,782,397 A | 7/1998 | Koukline | |
| 5,785,232 A | 7/1998 | Vidal et al. | |
| 5,797,536 A | 8/1998 | Smith et al. | |
| 5,797,537 A | 8/1998 | Oberlin et al. | |
| 5,797,538 A | 8/1998 | Heaton et al. | |
| 5,799,857 A | 9/1998 | Robertson et al. | |
| 5,810,855 A | 9/1998 | Rayburn et al. | |
| 5,814,057 A | 9/1998 | Oi et al. | |
| 5,820,009 A | 10/1998 | Melling et al. | |
| 5,826,776 A | 10/1998 | Schulze et al. | |
| 5,829,662 A | 11/1998 | Allen et al. | |
| 5,833,695 A | 11/1998 | Yoon | |
| 5,836,503 A | 11/1998 | Ehrenfels et al. | |
| 5,839,639 A | 11/1998 | Sauer et al. | |
| 5,855,311 A | 1/1999 | Hamblin et al. | |
| 5,855,583 A | 1/1999 | Wang et al. | |
| 5,865,361 A | 2/1999 | Milliman et al. | |
| 5,868,760 A | 2/1999 | McGuckin, Jr. | |
| 5,871,135 A | 2/1999 | Williamson, IV et al. | |
| 5,897,562 A | 4/1999 | Bolanos et al. | |
| 5,901,895 A | 5/1999 | Heaton et al. | |
| 5,908,427 A | 6/1999 | McKean et al. | |
| 5,911,353 A | 6/1999 | Bolanos et al. | |
| 5,915,616 A | 6/1999 | Viola et al. | |
| 5,919,198 A | 7/1999 | Graves, Jr. et al. | |
| 5,937,951 A | 8/1999 | Izuchukwu et al. | |
| 5,941,442 A | 8/1999 | Geiste et al. | |
| 5,954,259 A | 9/1999 | Viola et al. | |
| 5,964,774 A | 10/1999 | McKean et al. | |
| 6,010,054 A | 1/2000 | Johnson et al. | |
| 6,024,748 A | 2/2000 | Manzo et al. | |
| 6,032,849 A | 3/2000 | Mastri et al. | |
| 6,045,560 A | 4/2000 | McKean et al. | |
| 6,053,390 A | 4/2000 | Green et al. | |
| 6,063,097 A | 5/2000 | Oi et al. | |
| 6,083,234 A | 7/2000 | Nicholas et al. | |
| 6,083,242 A | 7/2000 | Cook | |
| 6,086,600 A | 7/2000 | Kortenbach | |
| 6,099,551 A | 8/2000 | Gabbay | |
| 6,102,271 A | 8/2000 | Longo et al. | |
| 6,117,148 A | 9/2000 | Ravo et al. | |
| 6,119,913 A | 9/2000 | Adams et al. | |
| 6,126,058 A | 10/2000 | Adams et al. | |
| 6,142,933 A | 11/2000 | Longo et al. | |
| 6,159,200 A * | 12/2000 | Verdura et al. | 606/1 |
| 6,171,330 B1 | 1/2001 | Benchetrit | |
| 6,193,129 B1 | 2/2001 | Bittner et al. | |
| 6,202,914 B1 | 3/2001 | Geiste et al. | |
| 6,241,139 B1 | 6/2001 | Milliman et al. | |
| 6,250,532 B1 | 6/2001 | Green et al. | |
| 6,258,107 B1 | 7/2001 | Balázs et al. | |
| 6,264,086 B1 | 7/2001 | McGuckin, Jr. | |
| 6,264,087 B1 | 7/2001 | Whitman | |
| 6,273,897 B1 | 8/2001 | Dalessandro et al. | |
| 6,293,927 B1 | 9/2001 | McGuckin, Jr. | |
| 6,302,311 B1 | 10/2001 | Adams et al. | |
| 6,315,184 B1 | 11/2001 | Whitman | |
| 6,325,810 B1 | 12/2001 | Hamilton et al. | |
| 6,330,965 B1 | 12/2001 | Milliman et al. | |
| 6,387,113 B1 | 5/2002 | Hawkins et al. | |
| 6,398,797 B2 | 6/2002 | Bombard et al. | |
| RE37,814 E | 8/2002 | Allgeyer | |
| 6,436,107 B1 | 8/2002 | Wang et al. | |
| 6,440,146 B2 | 8/2002 | Nicholas et al. | |
| 6,443,973 B1 | 9/2002 | Whitman | |
| 6,488,196 B1 | 12/2002 | Fenton, Jr. | |
| 6,488,197 B1 | 12/2002 | Whitman | |
| 6,491,201 B1 | 12/2002 | Whitman | |
| 6,503,257 B2 | 1/2003 | Grant et al. | |
| 6,503,259 B2 | 1/2003 | Huxel et al. | |
| 6,505,768 B2 | 1/2003 | Whitman | |
| 6,517,565 B1 | 2/2003 | Whitman et al. | |
| 6,517,566 B1 | 2/2003 | Hovland et al. | |
| 6,551,333 B2 | 4/2003 | Kuhns et al. | |
| 6,578,751 B2 | 6/2003 | Hartwick | |
| 6,588,643 B2 | 7/2003 | Bolduc et al. | |
| 6,592,597 B2 | 7/2003 | Grant et al. | |
| 6,601,749 B2 | 8/2003 | Sullivan et al. | |
| 6,616,686 B2 | 9/2003 | Coleman et al. | |
| 6,619,529 B2 | 9/2003 | Green et al. | |
| 6,629,630 B2 | 10/2003 | Adams | |
| 6,629,988 B2 | 10/2003 | Weadock | |
| 6,638,285 B2 | 10/2003 | Gabbay | |
| 6,644,532 B2 | 11/2003 | Green et al. | |
| 6,656,193 B2 | 12/2003 | Grant et al. | |
| 6,681,978 B2 | 1/2004 | Geiste et al. | |
| 6,681,979 B2 | 1/2004 | Whitman | |
| 6,695,199 B2 | 2/2004 | Whitman | |
| 6,698,643 B2 | 3/2004 | Whitman | |
| 6,716,233 B1 | 4/2004 | Whitman | |
| 6,722,552 B2 | 4/2004 | Fenton, Jr. | |
| 6,726,697 B2 | 4/2004 | Nicholas et al. | |
| 6,749,600 B1 | 6/2004 | Levy | |
| 6,755,338 B2 | 6/2004 | Hahnen et al. | |
| 6,769,594 B2 | 8/2004 | Orban, III | |
| 6,773,438 B1 | 8/2004 | Knodel et al. | |
| 6,786,382 B1 | 9/2004 | Hoffman | |
| 6,805,273 B2 | 10/2004 | Bilotti et al. | |
| 6,817,508 B1 | 11/2004 | Racenet et al. | |
| 6,817,509 B2 | 11/2004 | Geiste et al. | |
| 6,821,284 B2 | 11/2004 | Sturtz et al. | |
| 6,830,174 B2 | 12/2004 | Hillstead et al. | |
| 6,843,403 B2 | 1/2005 | Whitman | |
| RE38,708 E | 3/2005 | Bolanos et al. | |
| 6,866,178 B2 | 3/2005 | Adams et al. | |
| 6,872,214 B2 | 3/2005 | Sonnenschein et al. | |
| 6,874,669 B2 | 4/2005 | Adams et al. | |
| 6,877,647 B2 | 4/2005 | Green et al. | |
| 6,905,057 B2 | 6/2005 | Swayze et al. | |
| 6,913,608 B2 | 7/2005 | Liddicoat et al. | |
| 6,939,358 B2 | 9/2005 | Palacios et al. | |
| 6,945,444 B2 | 9/2005 | Gresham et al. | |
| 6,953,138 B1 | 10/2005 | Dworak et al. | |
| 6,953,139 B2 | 10/2005 | Milliman et al. | |
| 6,959,851 B2 | 11/2005 | Heinrich | |
| 6,959,852 B2 | 11/2005 | Shelton, IV et al. | |
| 6,960,220 B2 | 11/2005 | Marino et al. | |
| 6,964,363 B2 | 11/2005 | Wales et al. | |
| 6,978,921 B2 | 12/2005 | Shelton, IV et al. | |
| 6,978,922 B2 | 12/2005 | Bilotti et al. | |
| 6,981,628 B2 | 1/2006 | Wales | |
| 6,981,978 B2 | 1/2006 | Gannoe | |
| 6,986,451 B1 | 1/2006 | Mastri et al. | |
| 6,988,650 B2 | 1/2006 | Schwemberger et al. | |
| 6,997,931 B2 | 2/2006 | Sauer et al. | |
| 7,000,818 B2 | 2/2006 | Shelton, IV et al. | |
| 7,000,819 B2 | 2/2006 | Swayze et al. | |
| 7,008,435 B2 | 3/2006 | Cummins | |
| 7,032,798 B2 | 4/2006 | Whitman et al. | |
| 7,032,799 B2 | 4/2006 | Viola et al. | |
| 7,037,314 B2 | 5/2006 | Armstrong | |
| 7,044,352 B2 | 5/2006 | Shelton, IV et al. | |
| 7,044,353 B2 | 5/2006 | Mastri et al. | |
| 7,055,731 B2 | 6/2006 | Shelton, IV et al. | |
| 7,056,330 B2 | 6/2006 | Gayton | |
| 7,063,712 B2 | 6/2006 | Vargas et al. | |

| Patent No. | Date | Inventor |
|---|---|---|
| 7,066,944 B2 | 6/2006 | Laufer et al. |
| 7,070,083 B2 | 7/2006 | Jankowski |
| 7,077,856 B2 | 7/2006 | Whitman |
| 7,080,769 B2 | 7/2006 | Vresh et al. |
| 7,083,075 B2 | 8/2006 | Swayze et al. |
| 7,090,684 B2 | 8/2006 | McGuckin, Jr. et al. |
| 7,094,247 B2 | 8/2006 | Monassevitch et al. |
| 7,108,701 B2 | 9/2006 | Evens et al. |
| 7,108,709 B2 | 9/2006 | Cummins |
| 7,111,769 B2 | 9/2006 | Wales et al. |
| 7,114,642 B2 | 10/2006 | Whitman |
| 7,118,582 B1 | 10/2006 | Wang et al. |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,140,527 B2 | 11/2006 | Ehrenfels et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,156,863 B2 | 1/2007 | Sonnenschein et al. |
| 7,159,750 B2 | 1/2007 | Racenet et al. |
| 7,168,604 B2 | 1/2007 | Milliman et al. |
| 7,179,267 B2 | 2/2007 | Nolan et al. |
| 7,182,239 B1 * | 2/2007 | Myers ................ 227/175.1 |
| 7,188,758 B2 | 3/2007 | Viola et al. |
| 7,207,471 B2 | 4/2007 | Heinrich et al. |
| 7,207,472 B2 | 4/2007 | Wukusick et al. |
| 7,210,609 B2 | 5/2007 | Leiboff et al. |
| 7,213,736 B2 | 5/2007 | Wales et al. |
| 7,220,272 B2 | 5/2007 | Weadock |
| 7,225,964 B2 | 6/2007 | Mastri et al. |
| 7,234,624 B2 | 6/2007 | Gresham et al. |
| 7,237,708 B1 | 7/2007 | Guy et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,679 B2 | 9/2007 | McGuckin, Jr. et al. |
| 7,278,562 B2 | 10/2007 | Mastri et al. |
| 7,278,563 B1 | 10/2007 | Green |
| 7,296,724 B2 | 11/2007 | Green et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,060 B2 | 4/2008 | Milliman |
| 7,364,061 B2 | 4/2008 | Swayze et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,455,208 B2 | 11/2008 | Wales et al. |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,481,347 B2 | 1/2009 | Roy |
| 7,481,349 B2 | 1/2009 | Holsten et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,568,603 B2 | 8/2009 | Shelton, IV et al. |
| 7,568,604 B2 | 8/2009 | Ehrenfels et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,624,902 B2 | 12/2009 | Marczyk et al. |
| 7,631,793 B2 | 12/2009 | Rethy et al. |
| 7,637,409 B2 | 12/2009 | Marczyk |
| 7,644,848 B2 | 1/2010 | Swayze et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,699,204 B2 | 4/2010 | Viola |
| 7,717,312 B2 | 5/2010 | Beetel |
| 7,717,873 B2 | 5/2010 | Swick |
| 7,721,930 B2 | 5/2010 | McKenna et al. |
| 7,721,931 B2 | 5/2010 | Shelton, IV et al. |
| 7,721,934 B2 | 5/2010 | Shelton, IV et al. |
| 7,721,936 B2 | 5/2010 | Shelton, IV et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,627 B2 | 6/2010 | Orban, III et al. |
| 7,776,060 B2 | 8/2010 | Mooradian et al. |
| 7,780,054 B2 | 8/2010 | Wales |
| 7,780,685 B2 | 8/2010 | Hunt et al. |
| 7,784,662 B2 | 8/2010 | Wales et al. |
| 7,832,611 B2 | 11/2010 | Boyden et al. |
| 7,837,081 B2 | 11/2010 | Holsten et al. |
| 7,845,533 B2 | 12/2010 | Marczyk et al. |
| 7,846,149 B2 | 12/2010 | Jankowski |
| 7,896,897 B2 | 3/2011 | Gresham et al. |
| 7,909,221 B2 | 3/2011 | Viola et al. |
| 7,914,543 B2 | 3/2011 | Roth et al. |
| 7,922,063 B2 | 4/2011 | Zemlok et al. |
| 7,931,877 B2 | 4/2011 | Steffens et al. |
| 7,938,307 B2 | 5/2011 | Bettuchi |
| 7,942,890 B2 | 5/2011 | D'Agostino et al. |
| 7,950,560 B2 | 5/2011 | Zemlok et al. |
| 7,967,180 B2 | 6/2011 | Scirica |
| 8,002,795 B2 | 8/2011 | Beetel |
| 8,034,077 B2 | 10/2011 | Smith et al. |
| 8,038,046 B2 | 10/2011 | Smith et al. |
| 8,066,167 B2 | 11/2011 | Measamer et al. |
| D650,074 S | 12/2011 | Hunt et al. |
| 8,097,017 B2 | 1/2012 | Viola |

| Patent/Publication No. | Date | Inventor(s) |
|---|---|---|
| 8,123,103 B2 | 2/2012 | Milliman |
| 8,167,895 B2 | 5/2012 | D'Agostino et al. |
| 8,211,125 B2 | 7/2012 | Spivey |
| 2002/0013591 A1* | 1/2002 | Fleischman et al. .......... 606/155 |
| 2002/0117534 A1 | 8/2002 | Green et al. |
| 2003/0220660 A1 | 11/2003 | Kortenbach et al. |
| 2004/0006372 A1 | 1/2004 | Racenet et al. |
| 2004/0034369 A1 | 2/2004 | Sauer et al. |
| 2004/0094597 A1 | 5/2004 | Whitman et al. |
| 2004/0097987 A1 | 5/2004 | Pugsley et al. |
| 2004/0108357 A1 | 6/2004 | Milliman et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2004/0243151 A1 | 12/2004 | Demmy et al. |
| 2004/0254608 A1 | 12/2004 | Huitema et al. |
| 2004/0267310 A1 | 12/2004 | Racenet et al. |
| 2005/0051163 A1* | 3/2005 | Deem et al. ............... 128/200.24 |
| 2005/0059997 A1 | 3/2005 | Bauman et al. |
| 2005/0070929 A1 | 3/2005 | Dalessandro et al. |
| 2005/0080454 A1 | 4/2005 | Drews et al. |
| 2005/0103819 A1 | 5/2005 | Racenet et al. |
| 2005/0119669 A1 | 6/2005 | Demmy |
| 2005/0125009 A1 | 6/2005 | Perry et al. |
| 2005/0143759 A1 | 6/2005 | Kelly |
| 2005/0145675 A1 | 7/2005 | Hartwick et al. |
| 2005/0177181 A1 | 8/2005 | Kagan et al. |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0240222 A1 | 10/2005 | Shipp |
| 2005/0245965 A1 | 11/2005 | Orban III et al. |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0085033 A1 | 4/2006 | Criscuolo et al. |
| 2006/0100643 A1 | 5/2006 | Laufer et al. |
| 2006/0108393 A1 | 5/2006 | Heinrich et al. |
| 2006/0161185 A1 | 7/2006 | Saadat et al. |
| 2006/0173470 A1 | 8/2006 | Oray et al. |
| 2006/0180634 A1 | 8/2006 | Shelton, IV et al. |
| 2006/0226196 A1 | 10/2006 | Hueil et al. |
| 2006/0235469 A1 | 10/2006 | Viola |
| 2006/0241692 A1 | 10/2006 | McGuckin, Jr. et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0034668 A1 | 2/2007 | Holsten et al. |
| 2007/0073341 A1 | 3/2007 | Smith et al. |
| 2007/0084897 A1 | 4/2007 | Shelton, IV et al. |
| 2007/0102472 A1 | 5/2007 | Shelton, IV |
| 2007/0102473 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175957 A1 | 8/2007 | Shelton, IV et al. |
| 2007/0175958 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0181632 A1 | 8/2007 | Milliman |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0203510 A1 | 8/2007 | Bettuchi |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0246505 A1 | 10/2007 | Pace-Floridia et al. |
| 2007/0270884 A1 | 11/2007 | Smith et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0035701 A1 | 2/2008 | Racenet et al. |
| 2008/0041917 A1 | 2/2008 | Racenet et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082114 A1 | 4/2008 | McKenna et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0140115 A1 | 6/2008 | Stopek |
| 2008/0154335 A1* | 6/2008 | Thrope et al. .................. 607/48 |
| 2008/0167522 A1 | 7/2008 | Giordano et al. |
| 2008/0167644 A1 | 7/2008 | Shelton et al. |
| 2008/0167671 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0172088 A1 | 7/2008 | Smith et al. |
| 2008/0185419 A1 | 8/2008 | Smith et al. |
| 2008/0197167 A1 | 8/2008 | Viola et al. |
| 2008/0210738 A1 | 9/2008 | Shelton et al. |
| 2008/0228029 A1 | 9/2008 | Mikkaichi et al. |
| 2008/0237296 A1 | 10/2008 | Boudreaux et al. |
| 2008/0251568 A1 | 10/2008 | Zemlok et al. |
| 2008/0251569 A1 | 10/2008 | Smith et al. |
| 2008/0283570 A1 | 11/2008 | Boyden et al. |
| 2008/0290134 A1 | 11/2008 | Bettuchi et al. |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314955 A1 | 12/2008 | Boudreaux et al. |
| 2008/0314957 A1 | 12/2008 | Boudreaux |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0057369 A1 | 3/2009 | Smith et al. |
| 2009/0076534 A1 | 3/2009 | Shelton, IV et al. |
| 2009/0108048 A1 | 4/2009 | Zemlok et al. |
| 2009/0114701 A1 | 5/2009 | Zemlok et al. |
| 2009/0149871 A9 | 6/2009 | Kagan et al. |
| 2009/0200355 A1 | 8/2009 | Baxter, III et al. |
| 2009/0206123 A1 | 8/2009 | Doll et al. |
| 2009/0206124 A1 | 8/2009 | Hall et al. |
| 2009/0206125 A1 | 8/2009 | Huitema et al. |
| 2009/0206126 A1 | 8/2009 | Huitema et al. |

| | | |
|---|---|---|
| 2009/0206128 A1 | 8/2009 | Hueil et al. |
| 2009/0206129 A1 | 8/2009 | Doll et al. |
| 2009/0206130 A1 | 8/2009 | Hall et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206134 A1 | 8/2009 | Swayze et al. |
| 2009/0206135 A1 | 8/2009 | Hall et al. |
| 2009/0206136 A1 | 8/2009 | Moore et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0289096 A1 | 11/2009 | Shelton, IV et al. |
| 2010/0001036 A1 | 1/2010 | Marczyk et al. |
| 2010/0012704 A1 | 1/2010 | Tarinelli Racenet et al. |
| 2010/0032470 A1 | 2/2010 | Hess et al. |
| 2010/0065605 A1 | 3/2010 | Shelton, IV et al. |
| 2010/0065609 A1 | 3/2010 | Schwemberger |
| 2010/0069942 A1 | 3/2010 | Shelton, IV |
| 2010/0072251 A1 | 3/2010 | Baxter, III et al. |
| 2010/0072252 A1 | 3/2010 | Baxter, III et al. |
| 2010/0072253 A1 | 3/2010 | Baxter, III et al. |
| 2010/0072254 A1 | 3/2010 | Aranyi et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089972 A1 | 4/2010 | Marczyk |
| 2010/0089974 A1 | 4/2010 | Shelton, IV |
| 2010/0096435 A1 | 4/2010 | Fuchs et al. |
| 2010/0108740 A1 | 5/2010 | Pastorelli et al. |
| 2010/0108741 A1 | 5/2010 | Hessler et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0163598 A1 | 7/2010 | Belzer |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0200637 A1 | 8/2010 | Beetel |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0230465 A1 | 9/2010 | Smith et al. |
| 2010/0243707 A1 | 9/2010 | Olson et al. |
| 2010/0243708 A1 | 9/2010 | Aranyi et al. |
| 2010/0243709 A1 | 9/2010 | Hess et al. |
| 2010/0258611 A1 | 10/2010 | Smith et al. |
| 2010/0264193 A1 | 10/2010 | Huang et al. |
| 2010/0264194 A1 | 10/2010 | Huang et al. |
| 2010/0276471 A1 | 11/2010 | Whitman |
| 2010/0294827 A1 | 11/2010 | Boyden et al. |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308100 A1 | 12/2010 | Boudreaux |
| 2010/0312261 A1* | 12/2010 | Suzuki et al. ............ 606/153 |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0036887 A1 | 2/2011 | Zemlok et al. |
| 2011/0042441 A1 | 2/2011 | Shelton, IV et al. |
| 2011/0060363 A1 | 3/2011 | Hess et al. |
| 2011/0062212 A1 | 3/2011 | Shelton, IV et al. |
| 2011/0068145 A1 | 3/2011 | Bedi et al. |
| 2011/0068148 A1 | 3/2011 | Hall et al. |
| 2011/0084112 A1 | 4/2011 | Kostrzewski |
| 2011/0084113 A1 | 4/2011 | Bedi et al. |
| 2011/0084115 A1 | 4/2011 | Bedi et al. |
| 2011/0087276 A1 | 4/2011 | Bedi et al. |
| 2011/0087279 A1 | 4/2011 | Shah et al. |
| 2011/0101065 A1 | 5/2011 | Milliman |
| 2011/0114697 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0121051 A1 | 5/2011 | Shelton, IV et al. |
| 2011/0121052 A1 | 5/2011 | Shelton, IV et al. |
| 2011/0125176 A1 | 5/2011 | Yates et al. |
| 2011/0125177 A1 | 5/2011 | Yates et al. |
| 2011/0132962 A1 | 6/2011 | Hall et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139852 A1 | 6/2011 | Zingman |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155780 A1 | 6/2011 | Boudreaux |
| 2011/0155781 A1 | 6/2011 | Swensgard et al. |
| 2011/0155785 A1 | 6/2011 | Laurent et al. |
| 2011/0155787 A1 | 6/2011 | Baxter, III et al. |
| 2011/0163147 A1 | 7/2011 | Laurent et al. |
| 2011/0174860 A1 | 7/2011 | Shelton, IV et al. |
| 2011/0174863 A1 | 7/2011 | Shelton, IV et al. |
| 2011/0192882 A1 | 8/2011 | Hess et al. |
| 2011/0210156 A1 | 9/2011 | Smith et al. |
| 2011/0226837 A1 | 9/2011 | Baxter, III et al. |
| 2011/0233258 A1 | 9/2011 | Boudreaux |
| 2011/0253766 A1 | 10/2011 | Baxter, III et al. |
| 2011/0275901 A1 | 11/2011 | Shelton, IV |
| 2011/0276083 A1 | 11/2011 | Shelton, IV et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0290857 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295270 A1 | 12/2011 | Giordano et al. |
| 2011/0295295 A1 | 12/2011 | Shelton, IV et al. |
| 2012/0024934 A1 | 2/2012 | Shelton, IV et al. |
| 2012/0024935 A1 | 2/2012 | Shelton, IV et al. |
| 2012/0024936 A1 | 2/2012 | Baxter, III et al. |
| 2012/0029272 A1 | 2/2012 | Shelton, IV et al. |
| 2012/0029544 A1 | 2/2012 | Shelton, IV et al. |
| 2012/0029547 A1 | 2/2012 | Shelton, IV et al. |
| 2012/0046692 A1 | 2/2012 | Smith et al. |
| 2012/0061448 A1 | 3/2012 | Zingman |
| 2012/0071711 A1 | 3/2012 | Shelton, IV et al. |
| 2012/0071866 A1 | 3/2012 | Kerr et al. |
| 2012/0074196 A1 | 3/2012 | Shelton, IV et al. |
| 2012/0074198 A1 | 3/2012 | Huitema et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080333 A1 | 4/2012 | Woodard, Jr. et al. |
| 2012/0080334 A1 | 4/2012 | Shelton, IV et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080339 A1 | 4/2012 | Shelton, IV et al. |

| | | | |
|---|---|---|---|
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080475 A1 | 4/2012 | Smith et al. |
| 2012/0080477 A1 | 4/2012 | Leimbach et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080487 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0132450 A1 | 5/2012 | Timm et al. |
| 2012/0138660 A1 | 6/2012 | Shelton, IV |
| 2012/0160721 A1 | 6/2012 | Shelton, IV et al. |
| 2012/0175399 A1 | 7/2012 | Shelton et al. |
| 2012/0187179 A1 | 7/2012 | Gleiman |
| 2012/0199630 A1 | 8/2012 | Shelton, IV et al. |
| 2012/0199631 A1 | 8/2012 | Shelton, IV et al. |
| 2012/0199632 A1 | 8/2012 | Spivey et al. |
| 2012/0199633 A1 | 8/2012 | Shelton, IV et al. |
| 2012/0203247 A1 | 8/2012 | Shelton, IV et al. |
| 2012/0205421 A1 | 8/2012 | Shelton, IV |
| 2012/0211546 A1 | 8/2012 | Shelton, IV |

FOREIGN PATENT DOCUMENTS

| | | |
|---|---|---|
| CA | 2512960 A1 | 1/2006 |
| CA | 2514274 A1 | 1/2006 |
| CN | 1868411 A | 11/2006 |
| CN | 1915180 A | 2/2007 |
| CN | 101095621 A | 1/2008 |
| DE | 273689 C | 5/1914 |
| DE | 1775926 A | 1/1972 |
| DE | 9412228 | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| EP | 0122046 A1 | 10/1984 |
| EP | 0070230 B1 | 10/1985 |
| EP | 0387980 B1 | 10/1985 |
| EP | 0033548 B1 | 5/1986 |
| EP | 0276104 A2 | 7/1988 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0843906 B1 | 3/2000 |
| EP | 0552050 B1 | 5/2000 |
| EP | 0833592 B1 | 5/2000 |
| EP | 0830094 B1 | 9/2000 |
| EP | 1034747 A1 | 9/2000 |
| EP | 1034748 A1 | 9/2000 |
| EP | 0694290 81 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 0852480 B1 | 8/2003 |

| | | | | | | | |
|---|---|---|---|---|---|---|---|
| EP | 0891154 | B1 | 9/2003 | EP | 1300117 | B1 | 8/2007 |
| EP | 0813843 | B1 | 10/2003 | EP | 1813199 | A1 | 8/2007 |
| EP | 0873089 | B1 | 10/2003 | EP | 1813201 | A1 | 8/2007 |
| EP | 0856326 | B1 | 11/2003 | EP | 1813203 | A2 | 8/2007 |
| EP | 1374788 | A1 | 1/2004 | EP | 1813207 | A1 | 8/2007 |
| EP | 0741996 | B1 | 2/2004 | EP | 1813209 | A1 | 8/2007 |
| EP | 0814712 | B1 | 2/2004 | EP | 1487359 | B1 | 10/2007 |
| EP | 1402837 | A1 | 3/2004 | EP | 1599146 | B1 | 10/2007 |
| EP | 0705570 | B1 | 4/2004 | EP | 1839596 | A1 | 10/2007 |
| EP | 0959784 | B1 | 4/2004 | EP | 1402821 | B1 | 12/2007 |
| EP | 1407719 | A2 | 4/2004 | EP | 1872727 | A1 | 1/2008 |
| EP | 1086713 | B1 | 5/2004 | EP | 1897502 | A1 | 3/2008 |
| EP | 0996378 | B1 | 6/2004 | EP | 1330201 | B1 | 6/2008 |
| EP | 1426012 | A1 | 6/2004 | EP | 1702568 | B1 | 7/2008 |
| EP | 0833593 | B2 | 7/2004 | EP | 1943957 | A2 | 7/2008 |
| EP | 1442694 | A1 | 8/2004 | EP | 1943976 | A2 | 7/2008 |
| EP | 0888749 | B1 | 9/2004 | EP | 1593337 | B1 | 8/2008 |
| EP | 0959786 | B1 | 9/2004 | EP | 1970014 | A1 | 9/2008 |
| EP | 1459695 | A1 | 9/2004 | EP | 1980213 | A2 | 10/2008 |
| EP | 1473819 | A1 | 11/2004 | EP | 1759645 | B1 | 11/2008 |
| EP | 1477119 | A1 | 11/2004 | EP | 1990014 | A2 | 11/2008 |
| EP | 1479345 | A1 | 11/2004 | EP | 1693008 | B1 | 12/2008 |
| EP | 1479347 | A1 | 11/2004 | EP | 1759640 | B1 | 12/2008 |
| EP | 1479348 | A1 | 11/2004 | EP | 2000102 | A2 | 12/2008 |
| EP | 0754437 | B2 | 12/2004 | EP | 1736104 | B1 | 3/2009 |
| EP | 1025807 | 61 | 12/2004 | EP | 1749486 | B1 | 3/2009 |
| EP | 1001710 | B1 | 1/2005 | EP | 2039316 | A2 | 3/2009 |
| EP | 1520521 | A1 | 4/2005 | EP | 1721576 | B1 | 4/2009 |
| EP | 1520523 | A1 | 4/2005 | EP | 1733686 | B1 | 4/2009 |
| EP | 1520525 | A1 | 4/2005 | EP | 2044890 | A1 | 4/2009 |
| EP | 1522264 | A1 | 4/2005 | EP | 1550413 | B1 | 6/2009 |
| EP | 1523942 | A2 | 4/2005 | EP | 1745748 | B1 | 8/2009 |
| EP | 1550408 | A1 | 7/2005 | EP | 2090256 | A2 | 8/2009 |
| EP | 1557129 | A1 | 7/2005 | EP | 1813208 | B1 | 11/2009 |
| EP | 1064883 | B1 | 8/2005 | EP | 1607050 | B1 | 12/2009 |
| EP | 1067876 | B1 | 8/2005 | EP | 1566150 | B1 | 4/2010 |
| EP | 0870473 | B1 | 9/2005 | EP | 1813206 | B1 | 4/2010 |
| EP | 1157666 | B1 | 9/2005 | EP | 1769754 | B1 | 6/2010 |
| EP | 0880338 | B1 | 10/2005 | EP | 1535565 | B1 | 10/2010 |
| EP | 1158917 | B1 | 11/2005 | EP | 1702570 | B1 | 10/2010 |
| EP | 1344498 | B1 | 11/2005 | EP | 1785098 | B1 | 10/2010 |
| EP | 1330989 | B1 | 12/2005 | EP | 1627605 | B1 | 12/2010 |
| EP | 0771176 | B2 | 1/2006 | EP | 1813205 | B1 | 6/2011 |
| EP | 1621138 | A2 | 2/2006 | EP | 1785102 | B1 | 1/2012 |
| EP | 1621139 | A2 | 2/2006 | FR | 1112936 | A | 3/1956 |
| EP | 1621141 | A2 | 2/2006 | FR | 2765794 | A | 1/1999 |
| EP | 1621145 | A2 | 2/2006 | GB | 939929 | A | 10/1963 |
| EP | 1621151 | A2 | 2/2006 | GB | 1210522 | A | 10/1970 |
| EP | 1034746 | B1 | 3/2006 | GB | 1217159 | A | 12/1970 |
| EP | 1632191 | A2 | 3/2006 | GB | 1339394 | A | 12/1973 |
| EP | 1065981 | B1 | 5/2006 | GB | 2109241 | A | 6/1983 |
| EP | 1082944 | B1 | 5/2006 | GB | 2272159 | A | 5/1994 |
| EP | 1652481 | A2 | 5/2006 | GB | 2284242 | A | 5/1995 |
| EP | 1382303 | B1 | 6/2006 | GB | 2336214 | A | 10/1999 |
| EP | 1253866 | B1 | 7/2006 | GB | 2425903 | A | 11/2006 |
| EP | 1032318 | B1 | 8/2006 | JP | 58500053 | A | 1/1983 |
| EP | 1045672 | B1 | 8/2006 | JP | 61-98249 | A | 5/1986 |
| EP | 1617768 | B1 | 8/2006 | JP | 63-203149 | | 8/1988 |
| EP | 1693015 | A2 | 8/2006 | JP | 3-12126 | A | 1/1991 |
| EP | 1400214 | B1 | 9/2006 | JP | 5-212039 | A | 8/1993 |
| EP | 1702567 | A2 | 9/2006 | JP | 6007357 | A | 1/1994 |
| EP | 1129665 | B1 | 11/2006 | JP | 7051273 | A | 2/1995 |
| EP | 1400206 | B1 | 11/2006 | JP | 8033641 | A | 2/1996 |
| EP | 1721568 | A1 | 11/2006 | JP | 8229050 | A | 9/1996 |
| EP | 1256317 | B1 | 12/2006 | JP | 2000033071 | A | 2/2000 |
| EP | 1285633 | B1 | 12/2006 | JP | 2000171730 | A | 6/2000 |
| EP | 1728473 | A1 | 12/2006 | JP | 2000287987 | A | 10/2000 |
| EP | 1728475 | A2 | 12/2006 | JP | 2000325303 | A | 11/2000 |
| EP | 1479346 | B1 | 1/2007 | JP | 2001-514541 | A | 9/2001 |
| EP | 1484024 | B1 | 1/2007 | JP | 2001286477 | A | 10/2001 |
| EP | 1754445 | A2 | 2/2007 | JP | 2002143078 | A | 5/2002 |
| EP | 1759812 | A1 | 3/2007 | JP | 2002369820 | A | 12/2002 |
| EP | 1767163 | A1 | 3/2007 | JP | 2004-344663 | | 12/2004 |
| EP | 1769756 | A1 | 4/2007 | JP | 2005-028149 | A | 2/2005 |
| EP | 1769758 | A1 | 4/2007 | JP | 2005505322 | T | 2/2005 |
| EP | 1581128 | B1 | 5/2007 | JP | 2005103293 | A | 4/2005 |
| EP | 1785097 | A2 | 5/2007 | JP | 2005131163 | A | 5/2005 |
| EP | 1790293 | A2 | 5/2007 | JP | 2005131164 | A | 5/2005 |
| EP | 1800610 | A1 | 6/2007 | JP | 2005131173 | A | 5/2005 |

| | | | | | | | |
|---|---|---|---|---|---|---|---|
| JP | 2005131211 | A | 5/2005 | WO | WO 98/17180 | A1 | 4/1998 |
| JP | 2005131212 | A | 5/2005 | WO | WO 98/27880 | A1 | 7/1998 |
| JP | 2005137423 | A | 6/2005 | WO | WO 98/30153 | A1 | 7/1998 |
| JP | 2005152416 | A | 6/2005 | WO | WO 98/47436 | A1 | 10/1998 |
| JP | 2005-523105 | A | 8/2005 | WO | WO 99/03407 | A1 | 1/1999 |
| JP | 2005524474 | A | 8/2005 | WO | WO 99/03408 | A1 | 1/1999 |
| JP | 2006-281405 | A | 10/2006 | WO | WO 99/03409 | A1 | 1/1999 |
| RU | 2008830 | C1 | 3/1994 | WO | WO 99/12483 | A1 | 3/1999 |
| RU | 2187249 | C2 | 8/2002 | WO | WO 99/12487 | A1 | 3/1999 |
| RU | 2225170 | C2 | 3/2004 | WO | WO 99/12488 | A1 | 3/1999 |
| SU | 189517 | A | 1/1967 | WO | WO 99/15086 | A1 | 4/1999 |
| SU | 328636 | A | 9/1972 | WO | WO 99/15091 | A1 | 4/1999 |
| SU | 886900 | A1 | 12/1981 | WO | WO 99/23933 | A2 | 5/1999 |
| SU | 1333319 | A2 | 8/1987 | WO | WO 99/23959 | A1 | 5/1999 |
| SU | 1377053 | A1 | 2/1988 | WO | WO 99/25261 | A1 | 5/1999 |
| SU | 1561964 | A1 | 5/1990 | WO | WO 99/29244 | A1 | 6/1999 |
| SU | 1722476 | A1 | 3/1992 | WO | WO 99/34744 | A1 | 7/1999 |
| WO | WO 82/02824 | A1 | 9/1982 | WO | WO 99/45849 | A1 | 9/1999 |
| WO | WO 91/15157 | A1 | 10/1991 | WO | WO 99/48430 | A1 | 9/1999 |
| WO | WO 92/20295 | A1 | 11/1992 | WO | WO 99/51158 | A1 | 10/1999 |
| WO | WO 92/21300 | A1 | 12/1992 | WO | WO 00/24322 | A1 | 5/2000 |
| WO | WO 93/08755 | A1 | 5/1993 | WO | WO 00/24330 | A1 | 5/2000 |
| WO | WO 93/13718 | A1 | 7/1993 | WO | WO 00/41638 | A1 | 7/2000 |
| WO | WO 93/14690 | A1 | 8/1993 | WO | WO 00/48506 | A1 | 8/2000 |
| WO | WO 93/15648 | A1 | 8/1993 | WO | WO 00/53112 | A2 | 9/2000 |
| WO | WO 93/15850 | A1 | 8/1993 | WO | WO 00/54653 | A1 | 9/2000 |
| WO | WO 93/19681 | A1 | 10/1993 | WO | WO 00/57796 | A1 | 10/2000 |
| WO | WO 94/00060 | A1 | 1/1994 | WO | WO 00/64365 | A1 | 11/2000 |
| WO | WO 94/11057 | A1 | 5/1994 | WO | WO 00/72762 | A1 | 12/2000 |
| WO | WO 94/12108 | A1 | 6/1994 | WO | WO 00/72765 | A1 | 12/2000 |
| WO | WO 94/18893 | A1 | 9/1994 | WO | WO 01/03587 | A1 | 1/2001 |
| WO | WO 94/22378 | A1 | 10/1994 | WO | WO 01/05702 | A1 | 1/2001 |
| WO | WO 94/23659 | A1 | 10/1994 | WO | WO 01/10482 | A1 | 2/2001 |
| WO | WO 95/02369 | A1 | 1/1995 | WO | WO 01/35845 | A1 | 5/2001 |
| WO | WO 95/03743 | A1 | 2/1995 | WO | WO 01/54594 | A1 | 8/2001 |
| WO | WO 95/06817 | A1 | 3/1995 | WO | WO 01/58371 | A1 | 8/2001 |
| WO | WO 95/09576 | A1 | 4/1995 | WO | WO 01/62158 | A2 | 8/2001 |
| WO | WO 95/09577 | A1 | 4/1995 | WO | WO 01/62161 | A1 | 8/2001 |
| WO | WO 95/14436 | A1 | 6/1995 | WO | WO 01/62162 | A1 | 8/2001 |
| WO | WO 95/17855 | A1 | 7/1995 | WO | WO 01/62164 | A2 | 8/2001 |
| WO | WO 95/18383 | A1 | 7/1995 | WO | WO 01/62169 | A2 | 8/2001 |
| WO | WO 95/18572 | A1 | 7/1995 | WO | WO 01/78605 | A2 | 10/2001 |
| WO | WO 95/19739 | A1 | 7/1995 | WO | WO 01/91646 | A1 | 12/2001 |
| WO | WO 95/20360 | A1 | 8/1995 | WO | WO 02/07608 | A2 | 1/2002 |
| WO | WO 95/23557 | A1 | 9/1995 | WO | WO 02/07618 | A1 | 1/2002 |
| WO | WO 95/24865 | A1 | 9/1995 | WO | WO 02/17799 | A1 | 3/2002 |
| WO | WO 95/25471 | A3 | 9/1995 | WO | WO 02/19920 | A1 | 3/2002 |
| WO | WO 95/26562 | A1 | 10/1995 | WO | WO 02/19932 | A1 | 3/2002 |
| WO | WO 95/29639 | A1 | 11/1995 | WO | WO 02/30297 | A2 | 4/2002 |
| WO | WO 96/04858 | A1 | 2/1996 | WO | WO 02/32322 | A2 | 4/2002 |
| WO | WO 96/19151 | A1 | 6/1996 | WO | WO 02/36028 | A1 | 5/2002 |
| WO | WO 96/19152 | A1 | 6/1996 | WO | WO 02/43571 | A2 | 6/2002 |
| WO | WO 96/20652 | A1 | 7/1996 | WO | WO 02/058568 | A1 | 8/2002 |
| WO | WO 96/21119 | A1 | 7/1996 | WO | WO 02/060328 | A1 | 8/2002 |
| WO | WO 96/22055 | A1 | 7/1996 | WO | WO 02/067785 | A2 | 9/2002 |
| WO | WO 96/23448 | A1 | 8/1996 | WO | WO 02/098302 | A1 | 12/2002 |
| WO | WO 96/24301 | A1 | 8/1996 | WO | WO 03/000138 | A2 | 1/2003 |
| WO | WO 96/27337 | A1 | 9/1996 | WO | WO 03/001329 | A2 | 1/2003 |
| WO | WO 96/31155 | A1 | 10/1996 | WO | WO 03/013363 | A1 | 2/2003 |
| WO | WO 96/35464 | A1 | 11/1996 | WO | WO 03/015604 | A2 | 2/2003 |
| WO | WO 96/39085 | A1 | 12/1996 | WO | WO 03/020106 | A2 | 3/2003 |
| WO | WO 96/39086 | A1 | 12/1996 | WO | WO 03/020139 | A2 | 3/2003 |
| WO | WO 96/39087 | A1 | 12/1996 | WO | WO 03/024339 | A1 | 3/2003 |
| WO | WO 96/39088 | A1 | 12/1996 | WO | WO 03/079909 | A3 | 3/2003 |
| WO | WO 96/39089 | A1 | 12/1996 | WO | WO 03/030743 | A2 | 4/2003 |
| WO | WO 97/00646 | A1 | 1/1997 | WO | WO 03/037193 | A1 | 5/2003 |
| WO | WO 97/00647 | A1 | 1/1997 | WO | WO 03/047436 | A3 | 6/2003 |
| WO | WO 97/06582 | A1 | 2/1997 | WO | WO 03/055402 | A1 | 7/2003 |
| WO | WO 97/10763 | A1 | 3/1997 | WO | WO 03/057048 | A1 | 7/2003 |
| WO | WO 97/10764 | A1 | 3/1997 | WO | WO 03/057058 | A1 | 7/2003 |
| WO | WO 97/11648 | A2 | 4/1997 | WO | WO 03/063694 | A1 | 8/2003 |
| WO | WO 97/11649 | A1 | 4/1997 | WO | WO 03/077769 | A1 | 9/2003 |
| WO | WO 97/15237 | A1 | 5/1997 | WO | WO 03/079911 | A1 | 10/2003 |
| WO | WO 97/24073 | A1 | 7/1997 | WO | WO 03/082126 | A1 | 10/2003 |
| WO | WO 97/24993 | A1 | 7/1997 | WO | WO 03/088845 | A2 | 10/2003 |
| WO | WO 97/30644 | A1 | 8/1997 | WO | WO 03/090630 | A2 | 11/2003 |
| WO | WO 97/34533 | A1 | 9/1997 | WO | WO 03/094743 | A1 | 11/2003 |
| WO | WO 97/37598 | A1 | 10/1997 | WO | WO 03/094745 | A1 | 11/2003 |
| WO | WO 97/39688 | A2 | 10/1997 | WO | WO 03/094746 | A1 | 11/2003 |

| | | | |
|---|---|---|---|
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/147439 A1 | 12/2007 |
| WO | WO 2008/021969 A2 | 2/2008 |
| WO | WO 2008/039270 A1 | 4/2008 |
| WO | WO 2008/045383 A2 | 4/2008 |
| WO | WO 2008/089404 A2 | 7/2008 |
| WO | WO 2008/109125 A1 | 9/2008 |
| WO | WO 2010/063795 A1 | 6/2010 |

OTHER PUBLICATIONS

U.S. Appl. No. 12/621,667, filed Nov. 19, 2009.
U.S. Appl. No. 12/621,672, filed Nov. 19, 2009.
U.S. Appl. No. 12/621,683, filed Nov. 19, 2009.
U.S. Appl. No. 12/621,688, filed Nov. 19, 2009.
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, 2000, 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
International Search Report for PCT/US2010/057104, dated Apr. 8, 2011 included in PCT Publication WO 2011/063041 (49 pages).
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).

* cited by examiner

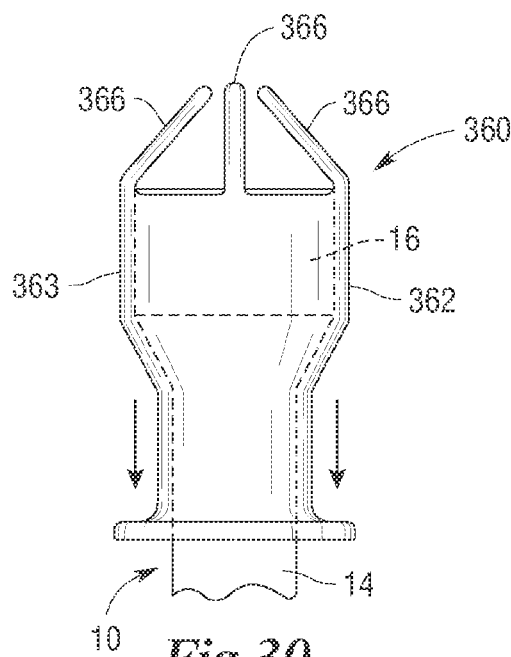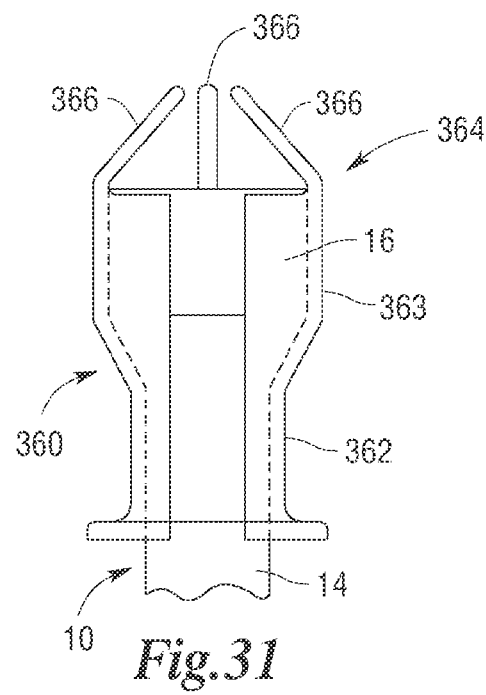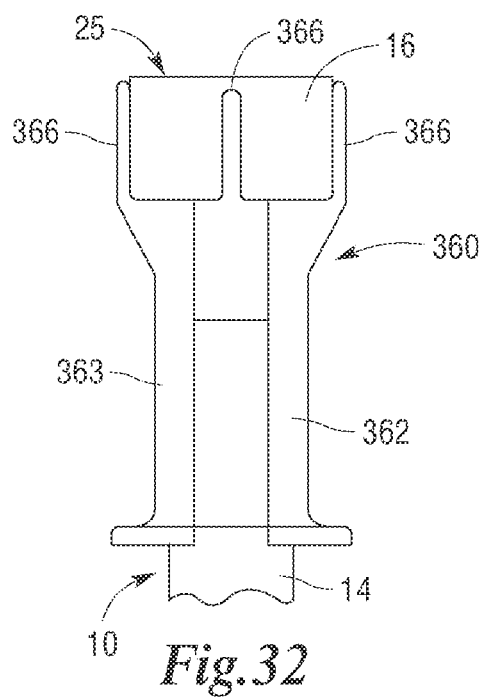

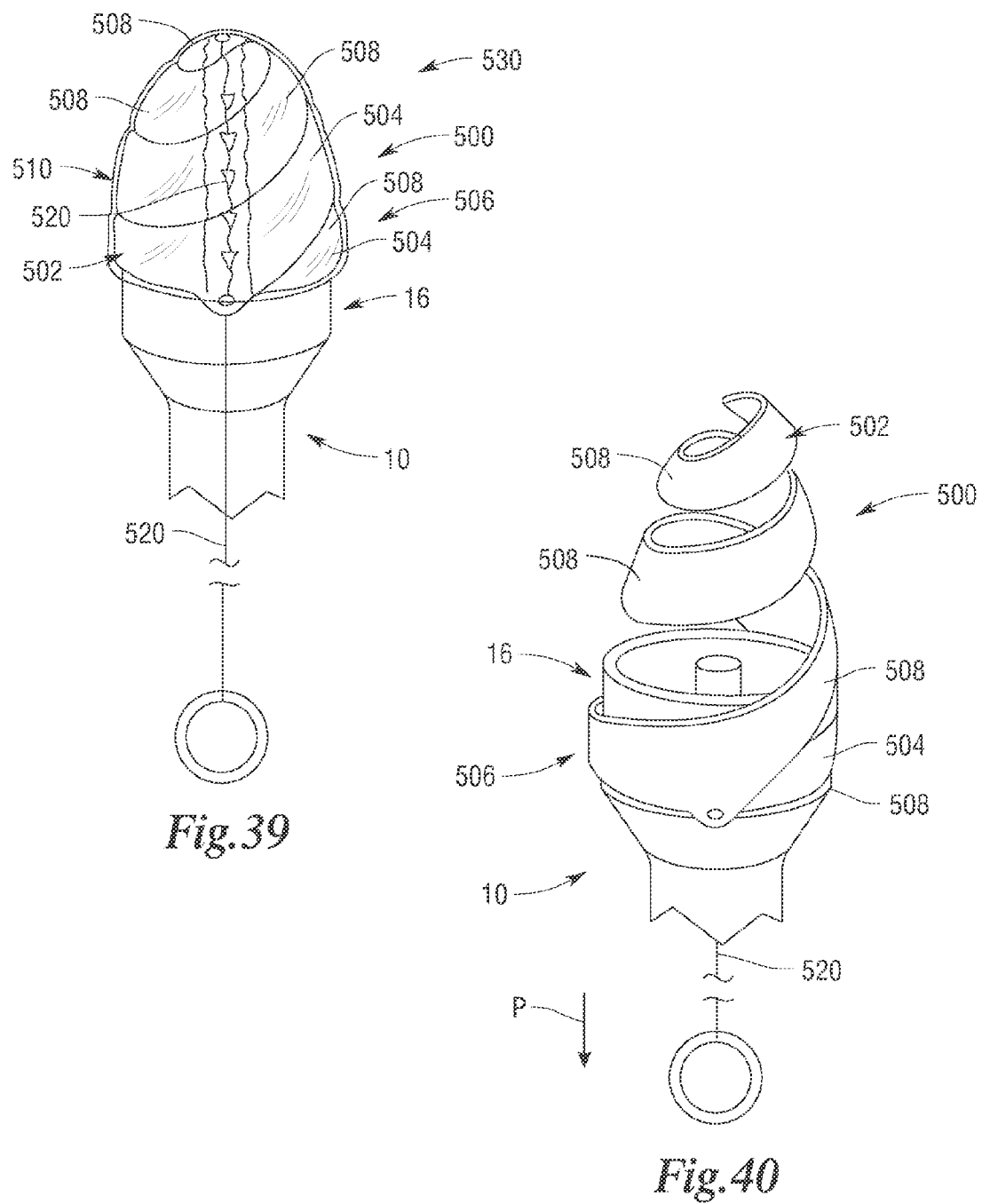

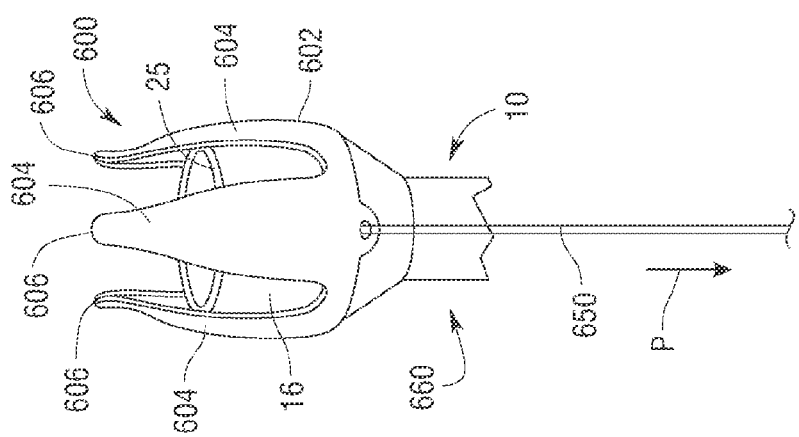
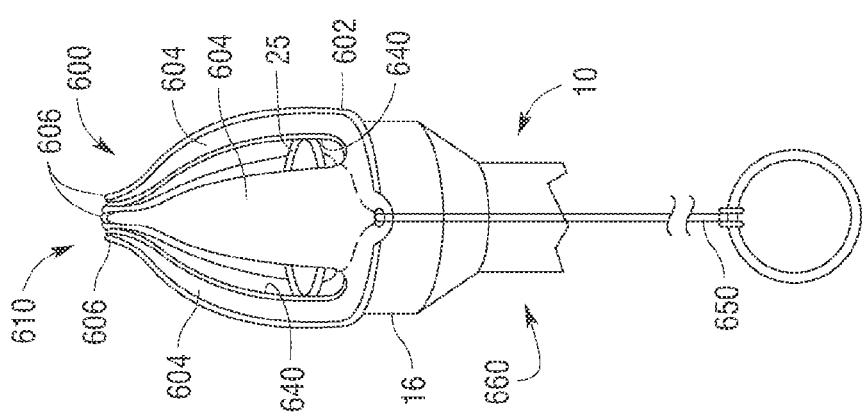
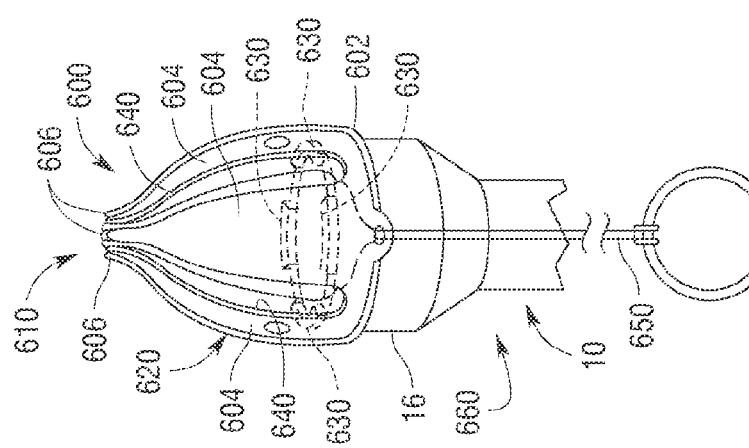

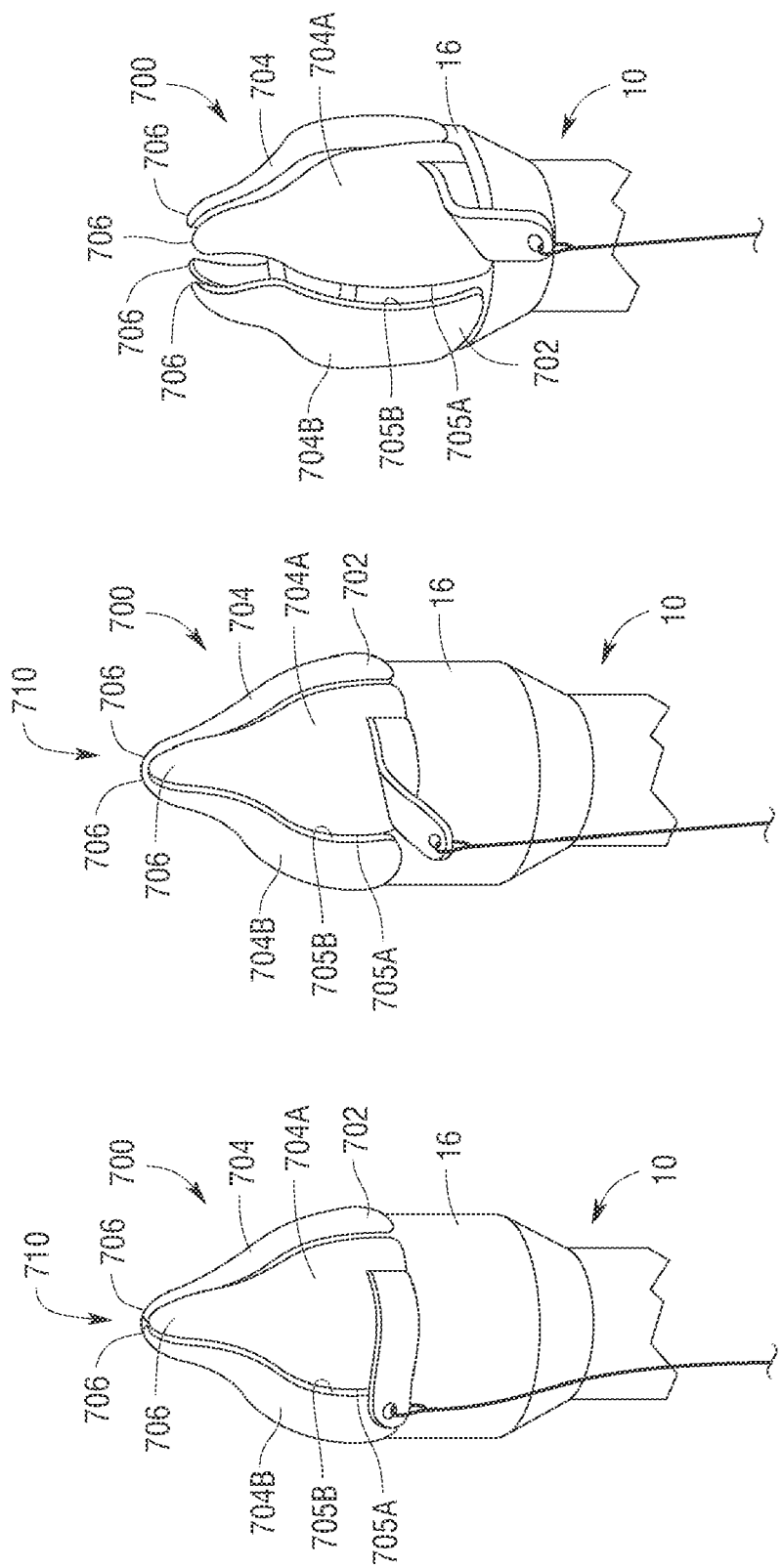

CIRCULAR STAPLER INTRODUCER WITH RIGID CAP ASSEMBLY CONFIGURED FOR EASY REMOVAL

FIELD OF THE INVENTION

The present invention generally relates to surgical staplers, and more particularly, to devices and methods for introducing a circular stapling device into the colon of a patient.

BACKGROUND

In certain types of surgical procedures, the use of surgical staples has become the preferred method of joining tissue and, as such, specially configured surgical staplers have been developed for these applications. For example, intra-luminal or circular staplers have been developed for use in surgical procedures involving the lower colon wherein sections of the lower colon are joined together after a diseased portion has been excised. Circular staplers useful for performing such procedures are disclosed, for example, in U.S. Pat. Nos. 5,104,025; 5,205,459; 5,285,945; and 5,309,927 which are each herein incorporated by reference in their respective entireties.

In general, a conventional circular stapler typically consists of an elongated shaft that has a proximal actuating mechanism and a distal stapling mechanism mounted to the elongated shaft. The distal stapling mechanism commonly consists of a fixed stapling cartridge that contains a plurality of staples configured in a concentric circular array. A round cutting knife is concentrically mounted in the cartridge interior to the staples for axial travel therein. Extending axially from the center of the cartridge is a movable trocar shaft that is adapted to have a staple anvil removably coupled thereto. The anvil is configured to form the ends of the staples as they are driven into it. The distance between a distal face of the staple cartridge and the staple anvil is commonly controlled by an adjustment mechanism that is mounted to the proximal end of the stapler shaft for controlling the axial movement of the trocar. Tissue that is clamped between the staple cartridge and the staple anvil is simultaneously stapled and cut when the actuating mechanism is activated by the surgeon.

When performing a lower colon procedure using a circular stapler, the intestine is typically stapled using a conventional surgical stapler with double rows of staples being emplaced on either side of the diseased portion of intestine to be removed. The target section is simultaneously cut as the adjoining end is stapled. After removing the diseased portion, the surgeon typically inserts the anvil into the proximal end of the lumen, proximal of the staple line. This is done by inserting the anvil head into an entry port cut into the proximal lumen by the surgeon. On occasion, the anvil can be placed transanally, by placing the anvil head on the distal end of the stapler and inserting the instrument through the rectum. The surgeon then ties the proximal end of the intestine to the anvil shaft using a suture or other conventional tying device. Next, the surgeon cuts excess tissue adjacent to the tie and the surgeon attaches the anvil to the trocar shaft of the stapler. The surgeon then closes the gap between the anvil and cartridge, thereby clamping the proximal and distal ends of the intestine in the gap. The surgeon next actuates the stapler causing several rows of staples to be driven through both ends of the intestine and formed, thereby joining the ends and forming a tubular pathway. Simultaneously, as the staples are driven and formed, the concentric circular knife blade is driven through the intestinal tissue ends, cutting the ends adjacent to the inner row of staples. The surgeon then withdraws the stapler from the intestine and the procedure is complete.

During such lower colon procedures, it may be difficult to insert the surgical stapler thru the anus and past the transverse folds in the rectal wall that protrude into the colon which are commonly referred to as the "Valves of Houston" and subsequently manipulated to the desired area. This problem is exacerbated when the stapler must be inserted without the anvil in position. In particular, the forward or distal end of most circular staplers comprises a relatively abrupt circular-shaped member designed to support a circular staple cartridge. Such blunt/abrupt shape makes it difficult to advance the forward end of the stapler past the Valves of Houston and other tissue.

Thus, the need exists for devices and methods for easily inserting a surgical stapler through a patient's anus into the lower colon or into other areas within the patient.

The foregoing discussion is intended only to illustrate some of the shortcomings present in the field of the invention at the time, and should not be taken as a disavowal of claim scope.

BRIEF SUMMARY

In connection with a general aspect of the present invention, there is provided an introducer for introducing a surgical circular stapler that has a handle portion, an elongated shaft that protrudes from the handle portion, and a stapling head that is coupled to the elongated shaft into a patient. In connection with various embodiments, the introducer comprises a hollow flexible sheath that has a distal end and an open proximal end. The hollow flexible sheath may be sized to receive the stapling head and at least a portion of the elongated shaft therein. A rigid cap assembly may be attached to the distal end of the hollow flexible sheath. The rigid cap assembly may be configured to selectively move between a closed position wherein a distal face of the stapling head is covered by the rigid cap assembly when the stapling head has been inserted therein to a fully inserted position and an open position wherein the cap assembly may be proximally withdrawn from around the stapling head and elongated shaft. The cap assembly may have a portion that is shaped to match a shape of a perimeter of a corresponding portion of the stapling head to enable the rigid cap assembly to pass proximally past the stapling head when being withdrawn therefrom.

In connection with another general aspect of the present invention, there is provided an introducer for introducing a surgical circular stapler that has a handle portion, an elongated shaft that protrudes from the handle portion, and a stapling head that is coupled to the elongated shaft into a patient. In connection with various embodiments the introducer comprises a hollow flexible sheath that has a distal end and an open proximal end. The hollow flexible sheath may be sized to receive the stapling head and at least a portion of the elongated shaft therein. A radially-openable barrel member may be attached to a distal end of the hollow flexible sheath that defines an opening for receiving the stapling head therein. A latch member may be oriented in engagement with a pair of opposed ends of the radially-openable barrel member. The latch member may be selectively movable from a latched position wherein the latch member engages the opposed ends of the barrel member and an unlatched position wherein the opposed ends may move radially away from each other. A rigid cap member may be hingably attached to the radially-openable barrel member and may be movable between a closed position wherein the rigid cap member is retained in a closed position covering a distal end of the opening in the barrel member and an open position wherein the rigid cap member is movable to a position exposing the distal end of the opening. The rigid cap member may have an underside that has a shape that matches a shape of a perimeter of a corresponding portion of the stapling head to enable the rigid cap member to pass proximally past the stapling head when being proximally withdrawn therefrom.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 30 is a side elevational view of another introducer embodiment of the present invention in a closed position;

FIG. 31 is another side elevational view of the introducer of FIG. 31;

FIG. 32 is another side elevational view of the introducer of FIGS. 30 and 31 in a closed position;

FIG. 39 is a partial perspective view of another introducer embodiment of the present invention attached to the stapling head of a circular stapler;

FIG. 40 is another partial perspective view of the introducer embodiment of FIG. 39 being unwound from the stapling head of the circular stapler;

FIG. 41 is a partial perspective view of another introducer embodiment of the present invention attached to the stapling head of a circular stapler;

FIG. 42 is a partial perspective view of another introducer embodiment of the present invention attached to the stapling head of a circular stapler;

FIG. 43 is another partial perspective view of the introducer of FIG. 42 being withdrawn proximally from the stapling head of the circular stapler;

FIG. 44 is a partial perspective view of another introducer embodiment of the present invention attached to the stapling head of a circular stapler;

FIG. 45 is another partial perspective view of the introducer embodiment of FIG. 44 wherein a release motion has been initially applied thereto; and FIG. 46 is another partial perspective view of the introducer of FIGS. 44 and 45 illustrating further application of the release motion thereto.

DETAILED DESCRIPTION

The Applicant of the present application also owns the U.S. Patent Applications identified below which were filed on even date herewith and which are each herein incorporated by reference in their respective entirety:

U.S. patent application Ser. No. 12/621,672, entitled "DEVICES AND METHODS FOR INTRODUCING A SURGICAL CIRCULAR STAPLING INSTRUMENT INTO A PATIENT";

U. S. patent application Ser. No. 12/621,683, entitled "CIRCULAR STAPLER INTRODUCER WITH RADIALLY-OPENABLE DISTAL END PORTION";

U. S. patent application Ser. No. 12/621,688, entitled "CIRCULAR STAPLER INTRODUCER WITH RIGID DISTAL END PORTION"; and U.S. patent application Ser. No. 12/621,667, entitled "CIRCULAR STAPLER INTRODUCER WITH MULTI-LUMEN SHEATH".

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Figure 1:
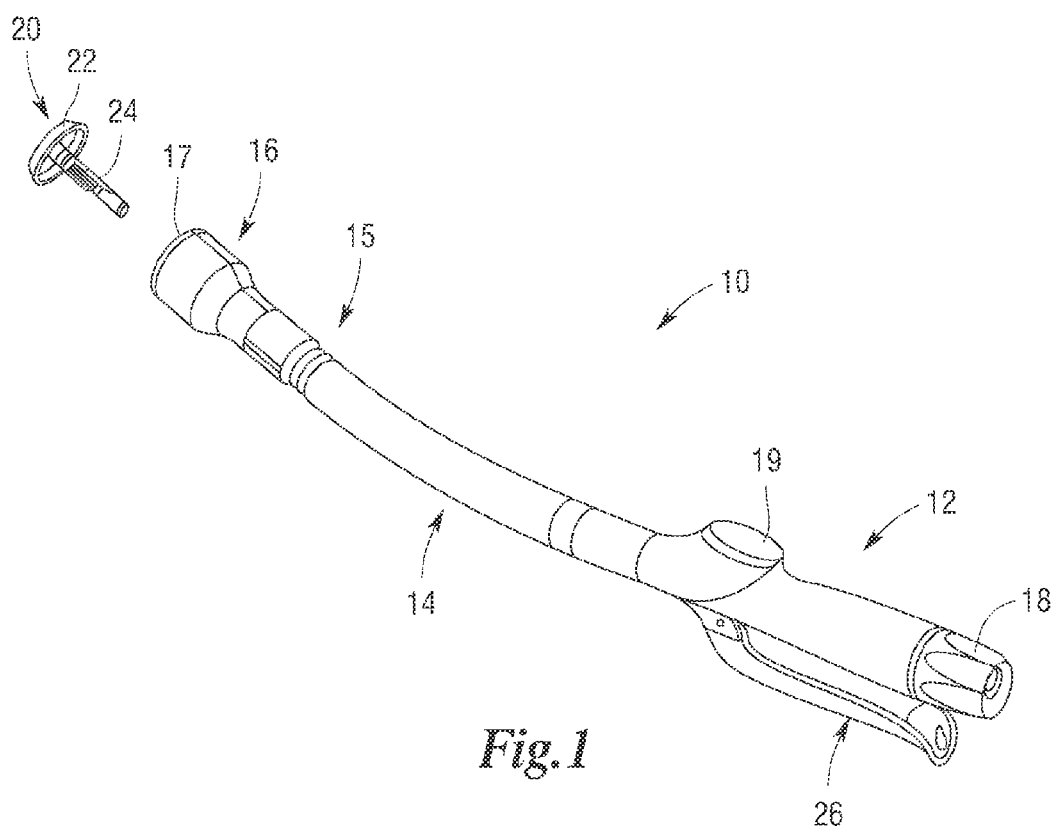
FIG. 1 is a perspective view of a surgical circular stapling instrument.
Figure 2:
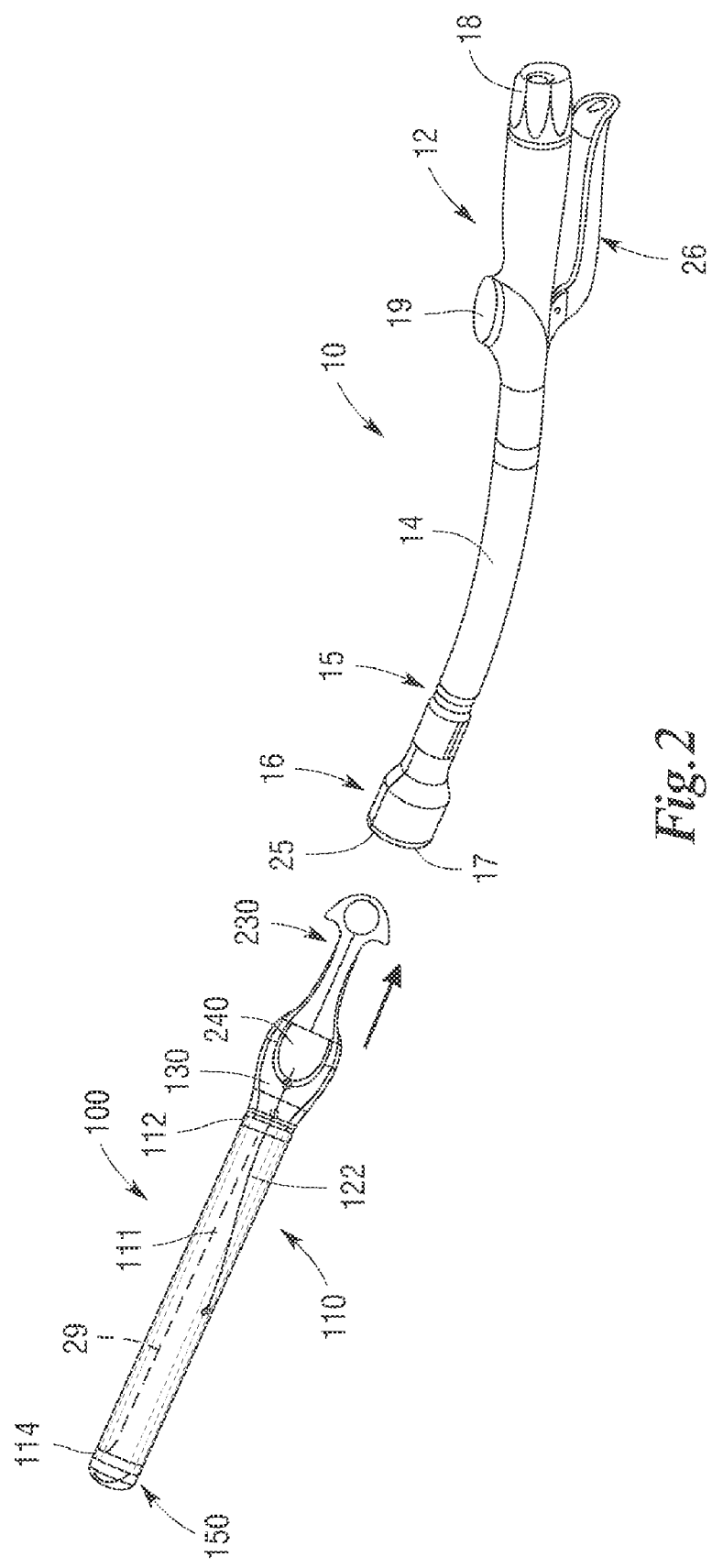
FIG. 2 is another perspective view of the circular surgical stapling instrument of FIG. 1 prior to the installation of an introducer embodiment of the present invention thereon.
Figure 3:
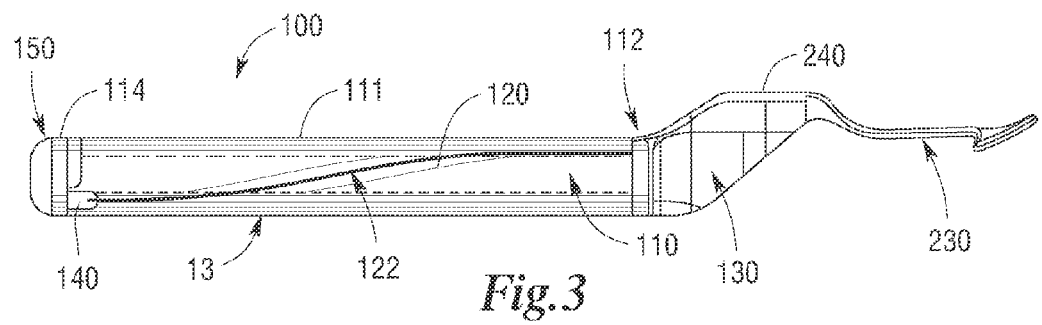
FIG. 3 is a side elevational view of an introducer embodiment of the present invention.
Figure 4:
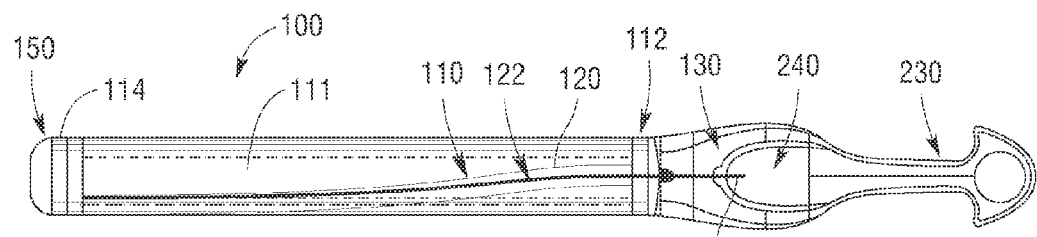
FIG. 4 is a top view of the introducer of FIG. 2.
Figure 5:
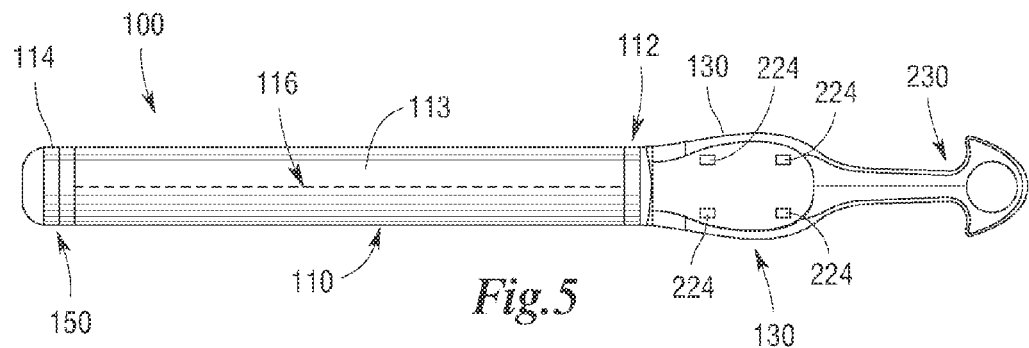
FIG. 5 is a top view of the introducer of FIGS. 3 and 4.

FIG. 1 illustrates a conventional circular stapler 10. The construction and operation of such circular staplers are generally known in the art. Thus, the specific components and features of such circular stapler will not be discussed in detail herein beyond what may be necessary to understand the construction and operation of the various embodiments of the present invention. As the present Detailed Description proceeds, those of ordinary skill in the art will understand that the various embodiments of the present invention may be effectively employed with a variety of different circular stapler configurations without departing from the spirit and scope of the present invention. Accordingly, the scope of protection afforded to the various embodiments of the present invention should not otherwise be limited to use with the exemplary circular stapler depicted herein.

As can be seen in FIG. 1, a conventional circular stapler 10 generally includes a handle portion 12 that has an elongated shaft 14 protruding therefrom. A stapling head 16 is coupled to the distal end 15 of the elongated shaft 14 and is configured to operably support a staple cartridge 17 and movable knife assembly (not shown) therein. The circular stapler 10 further includes an anvil 20 that has an anvil body 22. The anvil 20 has an anvil shaft 24 that is configured to be removably attached to a trocar (not shown) that is movably supported within the elongated shaft 14 of the circular stapler 10. Movement of the trocar is achieved by rotating an adjustment knob 18 that is located at the proximal end of the handle portion 12. An indicator panel 19 may be provided on the handle portion 12 to provide the user with an indication of the position of the body portion 22 of the anvil 20 relative to the staple cartridge 17. Thus, when the anvil shaft 24 is attached to the movable trocar, the position of the anvil body 22 relative to the staple cartridge 17 in the stapling head assembly 16 may be adjusted by rotating the adjustment knob 18. The stapling head 16 further supports a staple driver assembly (not shown), the operation of which is controlled by a trigger assembly 26 on the handle portion 12. Further details concerning the operation and assembly of the exemplary circular stapler 10, for example, may be gleaned from reference to U.S. patent application Ser. No. 12/408,905, filed Mar. 23, 2009, entitled "Circular Surgical Stapling Instrument With Anvil Locking System" to John P. Measamer, the disclosure of which is herein incorporated by reference in its entirety.

FIGS. 2-6 illustrate a circular stapler introducer 100 of the present invention that may be used in connection with a circular stapler 10. In various embodiments, the introducer 100 comprises an elongated hollow flexible sheath 110 that may be fabricated from, for example, a plastic material such as polyurethane blends, polyesters, polyethylene or polypropylene having a thickness of 0.004-0.015 inches and forms a first lumen 29 sized to be readily inserted over the elongated shaft 14 of a circular stapler 10. The sheath 110 has a distal end 114 and an open proximal end 112 as well as a top portion generally designated as 111 and a bottom portion 113. See FIG. 3. A handle assembly 130 may be attached to the open proximal end 112 by, for example, adhesive or ultrasonic welding, radio frequency (RF) welding or heat staking. The distal end 114 of the sheath 110 may be attached to a rigid cap assembly 130 by adhesive or by ultrasonic welding, radio frequency (RF) welding or heat staking. In various embodiments, a "weakened region" in the form of, for example, a perforated seam 116 may extend along the bottom portion 113 of the sheath 110 from the open proximal end 112 to the distal end 114. In addition, a second lumen 120 may be formed in the wall of the sheath 110 and extend from the open proximal end 112 to the distal end 114. In particular, the second lumen 120 may helically extend from the top portion 111 of the proximal end 112 to the bottom portion 113 at the distal end 114. The second lumen 120 may accommodate a release member 122 that extends from the handle assembly 130 to a latch member 140 that is movably supported in a distal end portion of the second lumen 120. In various embodiments, the release member 122 may comprise, for example, a suture. In other embodiments, the release member 122 may comprise a relatively thin flexible bar or similar member for transmitting a release motion to the latch member 140 attached thereto. The second lumen 120 may be formed in the wall of the sheath 110 by, for example, sewing, ultrasonic welding, radio frequency (RF) welding, heat staking, etc. The release member 122 and the latch member 140 may collectively form a release arrangement, generally designated as 121. See FIG. 10.

FIGS. 10-19, depict a rigid cap assembly 150 that may be used in connection with various embodiments of the present invention. The rigid cap assembly 150 may have a barrel member 152 that is attached to the distal end 114 of the sheath 110. The barrel member 152 comprises a partial ring-like member that has two opposed ends 154, 156. A rigid cap member 160 is "hingably attached" to the barrel member 152 by a tether 162. See FIG. 17. In various embodiments, the rigid cap assembly 150 is manufactured as a single injection molded piece that has significantly different physical properties. In various embodiments, for example, the rigid cap assembly 150 may be injection molded from polyurethane blends, polyesters, polyethylene or polypropylene.

As will be discussed in further detail below, the cap member 160 is made rigid by increasing its cross-sectional area while the tether 162 and barrel member 152 are preferably designed to allow significant deflection in specific directions by reducing their respective cross-sections. The cap member 160 has a relatively blunt distal surface 164 that is substantially smooth to minimize the force required to insert the introducer 100 and the portions of the circular stapler 10 housed therein through the patient's sphincter as well as to facilitate navigation of the device through the Valves of Houston and other anatomy. The underside 166 of the cap member 160 may have a series of reinforcing ribs 168 formed therein to increase its cross-sectional area and make the cap member 160 substantially rigid. See FIGS. 13 and 19.

Figure 13:
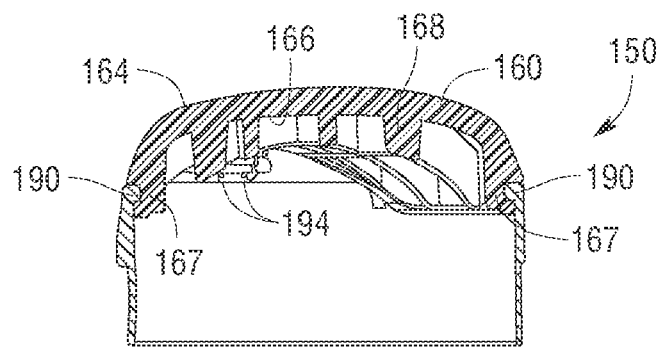
FIG. 13 is a cross-sectional view of a cap assembly embodiment of the present invention with the cap engaged with the barrel assembly.
Figures 14, 14A:
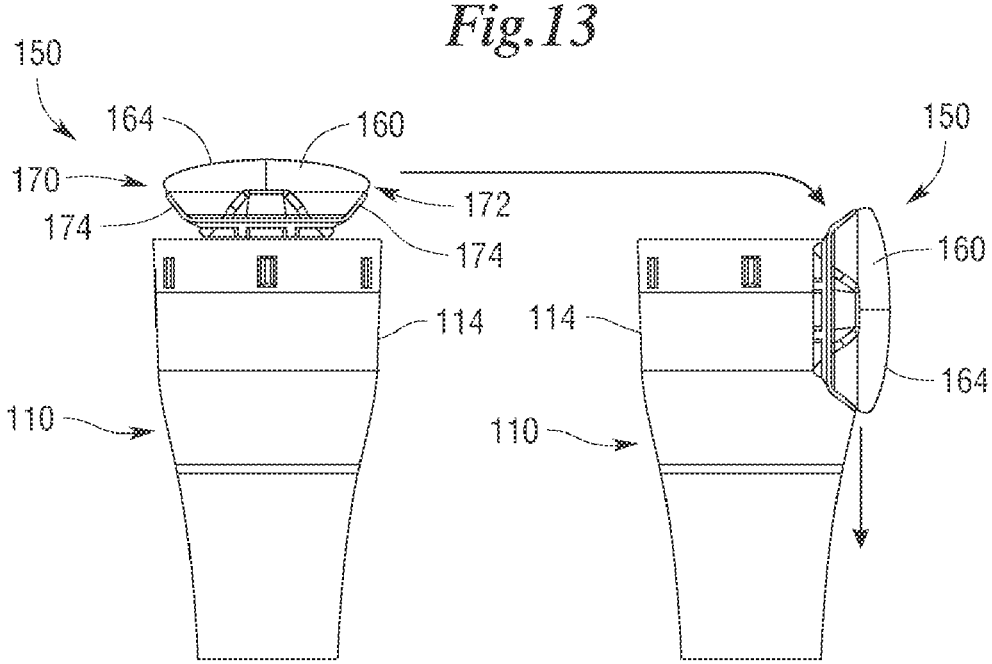
FIG. 14 is a partial side elevational view of a portion of a circular stapler and a cap of an introducer embodiment of the present invention.
FIG. 14A is another partial side elevational view of the circular stapler and cap with the cap sliding off the perimeter of the stapling head portion of the circular stapler.
Figure 15:
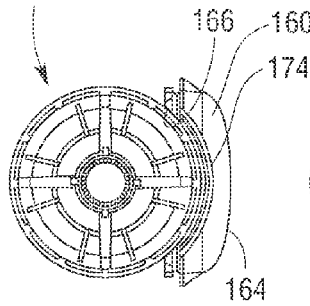
FIG. 15 is a top view of a cap assembly embodiment of the present invention with the cap in an open position.
Figure 16:
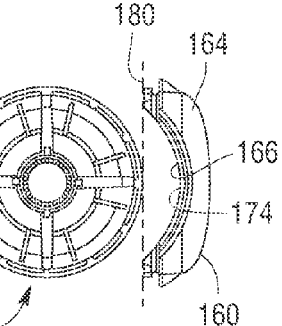
FIG. 16 is another top view of the cap assembly embodiment of FIG. 15 with a line illustrating a low profile cap embodiment.
Figure 17:
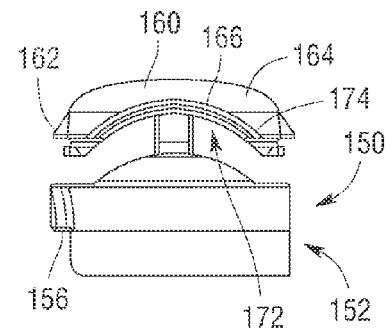
FIG. 17 is a side elevational view of the cap assembly embodiment of FIGS. 15 and 16.
Figure 18:
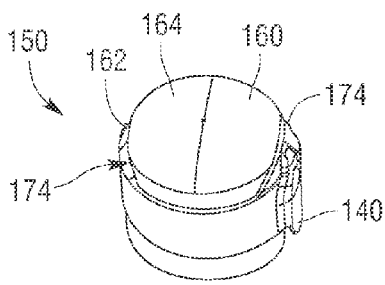
FIG. 18 is a top perspective view of a cap assembly embodiment of the present invention.

In various embodiments, the underside 166 of the cap member has a shape that substantially matches the shape of a portion of the perimeter of the stapling head 16. More specifically and as can be seen in FIG. 13, the underside 166, which is formed by reinforcing ribs 168, is arcuate in shape which matches a portion of the circular perimetrical shape of the stapling head 16 of the circular stapler 10. As can be further seen in FIG. 14, the cap member 160 has sides 170, 172 each has a cutout wall portion 174 that corresponds with the arcuate underside 166. Such arcuate underside 166 and cutout wall portions 174 enable the cap assembly 150 to pass proximally off the stapling head 16 when being proximally withdrawn over the circular stapler 10 to thereby reduce the radial distention of the bowel when the cap assembly 150 passes by the stapling head 16 of the circular stapler 10. For example, FIG. 16 provides an illustrative comparison between a cap assembly 150 with no arcuate underside 166 (represented by dotted line 180) and the cap assembly 150 with an arcuate underside 166. As illustrated, for one exemplary embodiment, the cap assembly without the arcuate underside has a 0.22" higher profile and would therefore further distend the bowel as it is withdrawn proximally over the stapling head 16.

Figure 10:
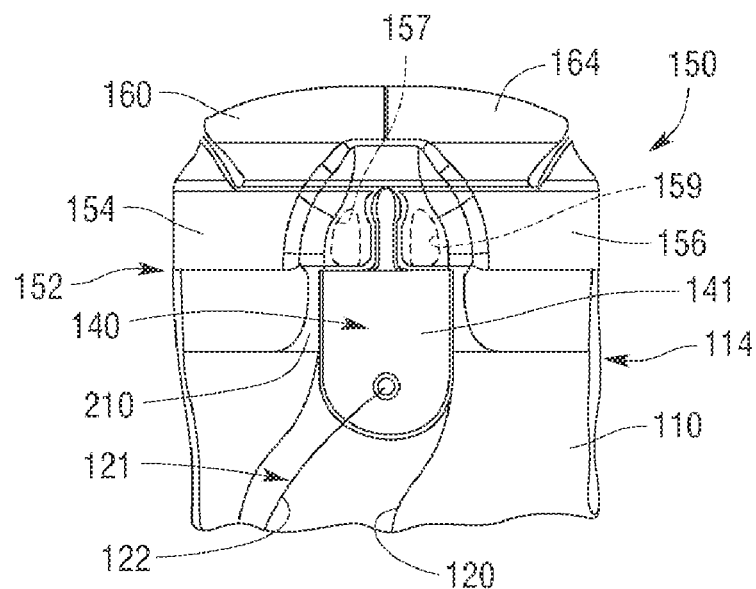
FIG. 10 is an elevational view of a cap assembly embodiment of the present invention.
Figure 20:
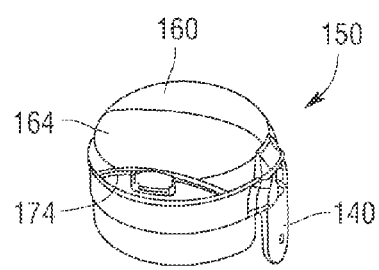
FIG. 20 is a top perspective view of another cap assembly embodiment of the present invention.
Figure 19:
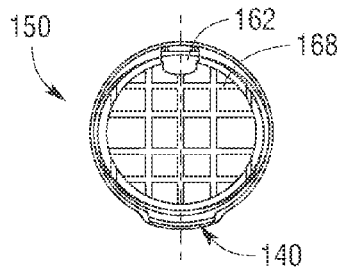
FIG. 19 is a bottom view of the cap assembly of FIG. 18.
Figure 21:
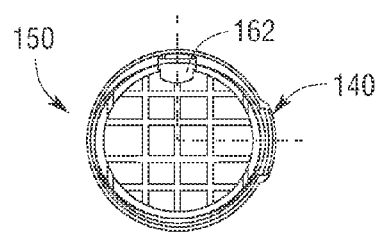
FIG. 21 is a bottom view of the cap assembly of FIG. 20.

In various embodiments, the tether 162 may be designed to be longer than the distance required to connect the cap member 160 to the barrel member 152 in the closed position (FIG. 10). That is, the tether 162 may coil inside the cap assembly 150 when the rigid cap portion 160 is retained in the closed position. Such arrangement permits the cap member 160 to follow a substantially curved path while passing over the corner of the stapling head 16 of the stapler 10 and to move independently from the barrel member 152 during removal. See FIGS. 14 and 14A. In one embodiment, the tether 162 is diametrically opposite from the location wherein the latch member 140 engages the opposed ends 154, 156 of the barrel member 152. See FIGS. 18 and 19. In an alternative embodiment, the tether 162 is located 90 degrees from the latch 140 member. See FIGS. 20 and 21.

Various embodiments of the cap assembly 150 employ features which work together to ensure that the cap member 160 does not open during the insertion process while retaining the ability to be easily opened and removed at the appropriate time. For example, as can be seen in FIG. 13, various embodiments of the cap assembly 150 may include an inwardly-extending retainer flange 190 that is formed on portions of the barrel member 152. The retainer flange 190 may be positioned to retainingly engage corresponding retention ribs 167 formed on the lower rim of the cap member 160. As can be seen in FIG. 13, a series of gussets 194 may be formed with the retainer flange 190 to further stabilize and rigidify the retention flange 190. Various cap member embodiments may include at least one retention rib on the cap member 160 to retainingly secure the cap member 160 in a closed position wherein the cap member 160 covers the distal face 25 of the stapling head 16 (FIG. 10). In various embodiments, a series of three ribs 200, 202, 204 may be formed on the two portions of the cap member 160 that are between the tether 162 and the arcuate cut out portions 174. The two outer ribs 200, 202, 204 may be provided with chamfered lead-out portions 206. See FIG. 12. Such chamfered lead out portions 206 interface with the retention flange 190 on the barrel member 152 and may serve to minimize the chances of the cap member 160 binding on the retention flange 190 during the unlatching process without significantly jeopardizing the ability of the rib 167 and retention flange 190 arrangement to carry loads during the insertion process.

Figure 11:
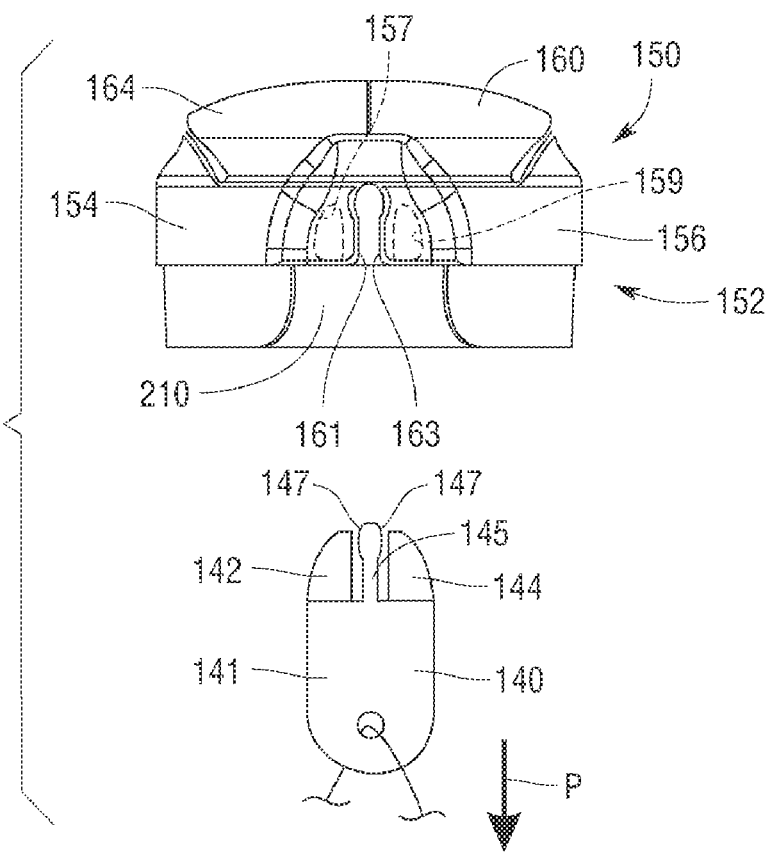
FIG. 11 is another elevational view of the cap assembly of FIG. 10 with the release latch removed therefrom.
Figure 12:
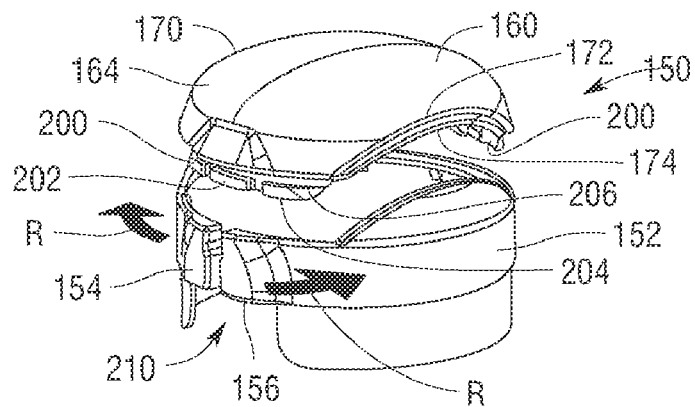
FIG. 12 is a perspective view of the cap assembly of FIGS. 8-11 with the release latch removed therefrom and the cap disengaged from the barrel assembly.

As can be seen in FIGS. 11 and 12, the opposed ends 154, 156 of the barrel member 152 are spaced from each other to define a latch region 210 for receiving the latch member 140 therein. The latch member 140 may be formed from a plastic material and have a body portion 141 that has a pair of distally protruding latch tabs 142, 144 formed thereon. See FIG. 11. The latch tabs 142, 144 are sized to extend into latch cavities 157, 159 formed in the opposing ends 154, 156 of the bar 152. See FIGS. 10 and 11. Thus, when the latch tabs 142, 144 are received in the latch cavities 157, 159, the barrel member 152 forms a radially-openable ring-like structure sized to accommodate the stapling head 16 of the circular stapler 10 therein. In various embodiments, when the barrel member 152 is latched in the closed position wherein the cap member 160 covers the distal face 25 of the stapling head 16 of the circular stapler 10, the cap member 160 may sit directly on the distal face 25 of the stapling head 16 of the circular stapler 10 without interfering with any of the staple pockets in the staple cartridge 17 support therein. Such arrangement permits the forces experienced by the cap member 160 during the insertion process to be transmitted directly to the stapling head 16 of the circular stapler 10 without the need for any force balancing or intermediate components.

Also in various embodiments, the release member 140 may be further formed with a release finger 145 that may serve to assist with radially opening the barrel member 152 when the latch member 140 is pulled proximally out of engagement with the opposed ends 154, 156 of the barrel member 152. More specifically and with reference to FIG. 11, the latch member 140 may be formed with a release finger 145 that is centrally disposed between the latch tabs 142, 144. The release finger 145 may be formed with cam portions 147 that are designed to engage cam surfaces 161, 163 formed on the opposed ends 154, 156 of the barrel member 152 such that, as the latch member 140 is pulled in the proximal direction "P", the cam portions 147 engage the cam surfaces 161, 163 to urge the opposed ends 154, 156 of the barrel member 152 radially apart from each other (represented by arrows "R", in FIG. 12.). Thus the latch member 140 is pulled in a direction (proximal direction "P") that is substantially perpendicular to the direction of motion "R" required to disengage the cap member 160 from the barrel member 152. When the latch member 140 is removed and the clinician continues to apply an additional withdrawal motion to the introducer 100, the opposed ends 154, 156 of the barrel member 152 are permitted to further radially separate and enable the cap member 160 to disengage from the barrel member 152 and move to an open position. In doing so, the cap member 160 may be permitted to rotate to a lateral open position to facilitate proximal movement of the cap assembly 150 over the stapling head 16 as the introducer 100 is withdrawn proximally from the patient. See FIG. 14.

Figure 7:
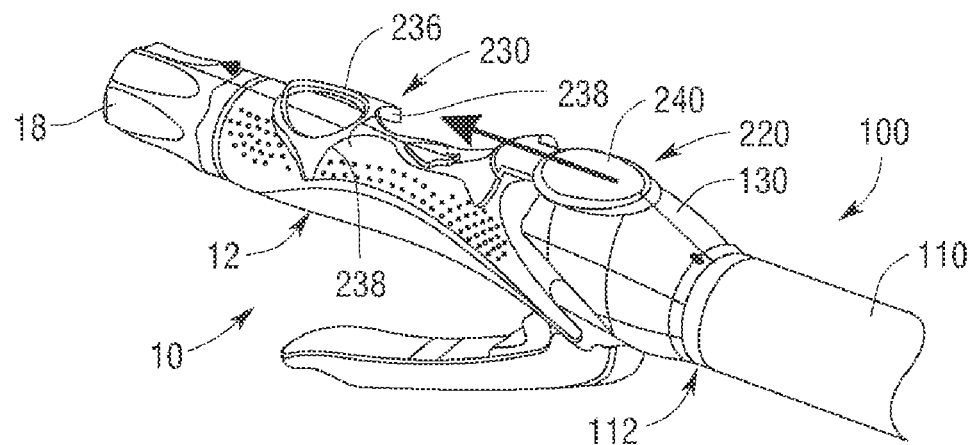
FIG. 7 is a partial perspective view of an introducer embodiment of the present invention installed on a circular stapling instrument.
Figure 8:
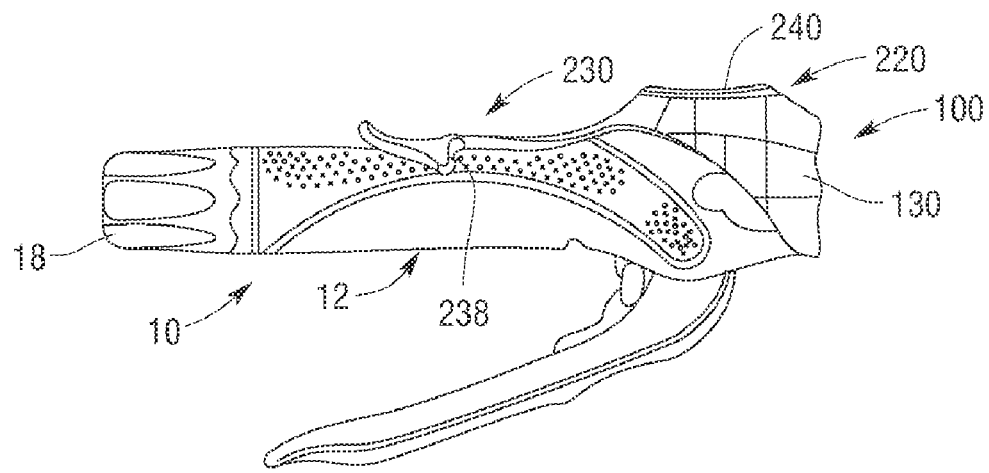
FIG. 8 is a partial side elevation view of the introducer and circular stapler of FIG. 7.
Figure 9:
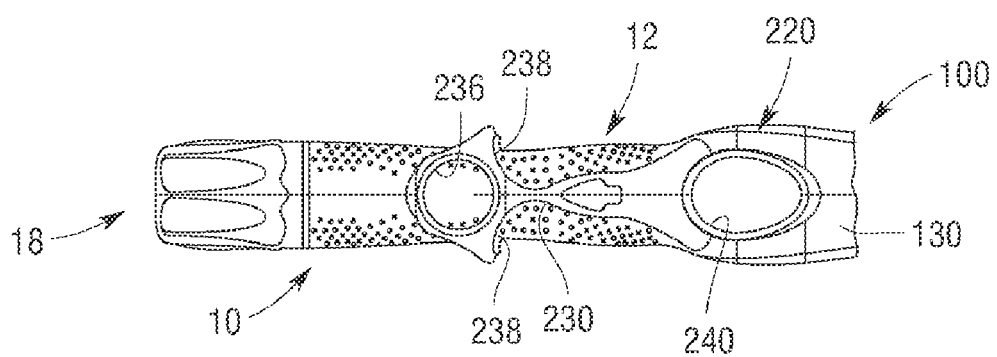
FIG. 9 is a partial top view of the introducer and circular stapler of FIGS. 7 and 8.

As can be seen in FIGS. 7-9, the handle assembly 130 may be designed to conform to the geometry of the handle portion 12 of the circular stapler 10 when the stapling head 16 has been inserted into the closed cap assembly 150 in a fully inserted position. For example, when a lower rim portion of the rigid cap member 160 is in contact with the distal face 25 of the stapling head 16, the stapling head 16 may be considered to be in the "fully inserted" position. More broadly, the circular stapler 10 may be considered to be in a fully inserted position when the distal face 25 is in contact with a portion of the rigid cap member 160.

In various embodiments, the handle assembly 130 may be configured in such a way as to prevent improper installation of the introducer 100 on the circular stapler 10. For example, the handle assembly 130 may be "orientation-specific" such that it includes features which mate with corresponding surfaces on the handle portion 12 of the circular stapler 10 when the stapling head has been inserted to the fully inserted position, while at the same time interfering with other surfaces if the introducer 100 is installed incorrectly. In addition, many circular staplers 10 include an indicator panel 19 that is located on the upper side of the handle portion. See FIG. 1. Such indicator panel 19 may, for example, provide the clinician with an indication of the position of the anvil 20 relative to the stapling head 16. In various embodiments, the handle portion 130 of the introducer 100 may be designed to cover or obscure the indicator panel 19 of the circular stapler 10. Such arrangement serves to ensure that the user is aware that the introducer 100 is installed on the stapler 10 and thereby prevents the user from attempting to fire the circular stapler 10 without first removing the introducer 100. For example, the handle assembly 130 includes a forward portion 220 that covers or otherwise obscures the indication panel 19 of the circular stapler 10.

Figure 6:
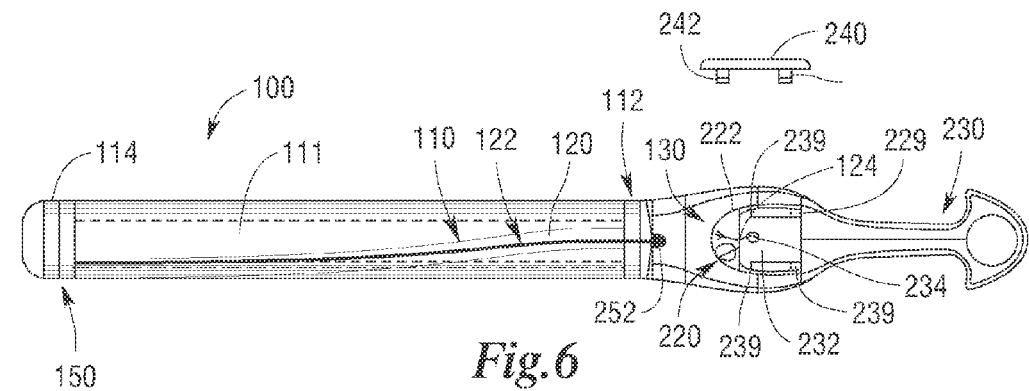
FIG. 6 is another top view of the introducer of FIGS. 2-5 with the cover panel removed from the handle assembly.

In various embodiments, the proximal end 124 of the release member 122 or suture is attached to a release slider 230. As can be seen in FIG. 6, the suture 122 may be attached to a forward tab portion 232 of the release slider 230 that is sized to be slidably received within a cavity 222 formed in the forward portion of the handle assembly 130. The forward tab portion 232 is slidably retained within the cavity 222 by a cover 240 that may be attached to the handle assembly 130 by a series of retainer tabs 242 that are oriented to snappingly engage corresponding snap cavities 224 in the handle assembly 130. See FIGS. 5 and 6

Various embodiments of the present invention may also incorporate a means for multiplying a proximal travel distance of the suture 122 relative to a distance that the release slider 230 is moved on the handle portion 12 of the circular stapler 10. For example, various embodiments may employ a pulley-type arrangement 250 to multiply the travel distance of the suture 122 relative the distance that the release slider 230 is moved in the proximal direction "P". Such arrangement may allow for greater travel to ensure the release of the cap member 160 without the need to lengthen the handle portion 130. For example, as shown in FIG. 6, the proximal end portion 124 of the suture 122 extends through a slot 252 in the handle assembly 130 and loops through a hole 234 in the forward slider tab 232. The end 124 of the suture 122 may then be attached to a fixed post 254 on the handle assembly 130

To facilitate easy removal of the introducer 100, the release slider 230 may be provided with a relatively "low profile" to enable the clinician to maintain a grip on the handle portion 12 of the stapler 10 without significantly changing their grip or method from what they would do with the circular stapler 10 alone. See FIGS. 7-9. Also, in various embodiments, the release slider 230 may be provided with a hole 236 and/or two lateral wing portions 238. Thus, this arrangement allows the clinician to apply force to the release slider 230 in the proximal direction "P" using either a single finger in the hole 236 or two fingers on the lateral wing portions 238.

As can also be seen in FIG. 6, the forward portion 220 of the handle assembly 130 may also be provided with stops 229 that are arranged to engage forward tabs 239 formed on the forward tab portion 232 of the release slider 230. Thus, in use, once the circular stapler 10 has been inserted into the introducer 100 to the fully inserted position and the stapler 10 and introducer 100 have been inserted to a desired position within the patient, the clinician may then pull the release slider 230 in a proximal direction to apply an amount of tension or release motion to the suture 122 to draw the latch member 140 to an unlatched position. Further pulling on the release slider 230 will result in the forward tabs 239 contacting the stops 229. Once the forward tabs 239 contact the stops 229, further pulling of the release slider 230 in the proximal direction causes the entire introducer 100 to move in the proximal direction. Such arrangement enables the entire introducer 100 to be decoupled from the stapler 10 and withdrawn from the patient by moving the release slider 230 in the proximal direction on the handle portion 12 of the circular stapler 10. The removal of the introducer 100 from the stapler 10 may be accomplished without removing the stapler 10 from the patient.

To use the introducer 100, the clinician simply inserts the circular stapler 10 into the sheath 110 to the fully inserted position and aligns the introducer 100 relative to the handle portion 12 such that the forward portion 220 of the handle portion 130 covers the indication panel 19 of the circular stapler 10. To aid in the insertion process, the stapling head 16 and shaft portion 14 of the circular stapler 10, as well as the cap assembly 150 and sheath 110 of the introducer 100, may be lubricated prior to commencing the insertion process. When the circular stapler 10 has been properly inserted into the introducer 100, the rim of the cap 160 which is engaged with the flange 190 of the barrel assembly 152 and thereby retained in the closed position as illustrated in FIGS. 3-6, 10 and 13, will rest on the stapling head 16 of the stapler 10. The user then inserts the stapler 10 and introducer 100 into a desired position in the colon. Once the stapler 10 is in a desired position, the clinician may pull on the release slider 230 in the proximal direction "P" which causes the suture 122 to pull the retainer latch 140 out of engagement with the ends 154, 156 of the barrel assembly 152. As the retainer latch 140 is drawn proximally, the cam surfaces 147 on the release finger 145 cooperate with the cam surfaces 161, 163 formed on the opposed ends 154, 156 of the barrel assembly 152 such that, as the release member 140 is pulled in the proximal direction "P", the ends 154, 156 are urged radially apart. Further pulling of the release slider 230 results in the forward tabs 232 contacting the stops 229 such that further pulling of the slider 230 results in the entire introducer 100 being pulled proximally over the circular stapler 10. Such pulling of the introducer 100 may cause the sheath 110 to separate along the line of perforations 116 and the cap 160 to move to an open position (FIGS. 14 and 15) to thereby enable the introducer 100 to be withdrawn from the patient prior to firing the stapler 10.

Figure 22:
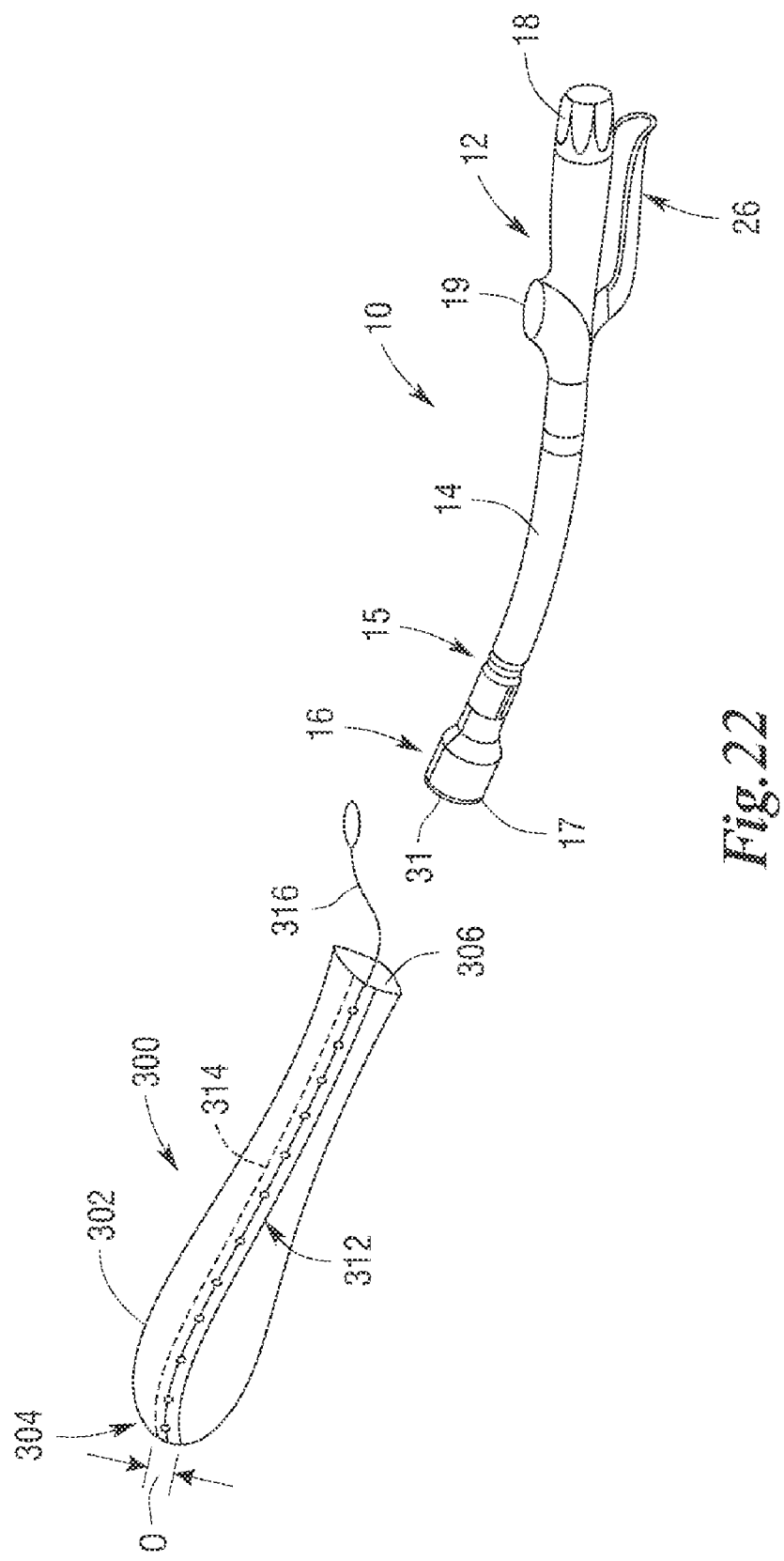
FIG. 22 is a perspective view of a circular surgical stapling instrument prior to the installation of another introducer embodiment of the present invention thereon.

FIG. 22 illustrates another introducer 300 of the present invention. In this embodiment, the introducer 300 comprises a hollow sheath 302 that has a closed end 304 and an open end 306 for insertion onto the circular stapler 10. The sheath 302 may be fabricated from a flexible material such as from those materials commonly employed to fabricate condoms. In one embodiment, the sheath 302 is fabricated from a single piece of material that has an elongate seam 310 that extends the length of the sheath 302. In particular, the sheath material is folded over such that the end 312 of the material overlaps end 314 of the material represented by distance "O" in FIG. 22. The ends 312, 314 are then stitched together by a suture 316 forming the seam 310. Thus, the sheath 302 is inserted over the stapling head 16 of the stapler 10 prior to insertion into the patient. After the stapler 10 and sheath 302 have been inserted into position, the sheath 302 may be removed by pulling the suture 316 to thereby release the seam 310 to permit the sheath 302 to be removed. In other embodiments, the sheath 302 is fabricated from two pieces of flexible material that are stitched together with two sutures 316 in the manner described above. To remove the sheath 302, the clinician simply pulls on one or both of the sutures 316.

Figure 23:
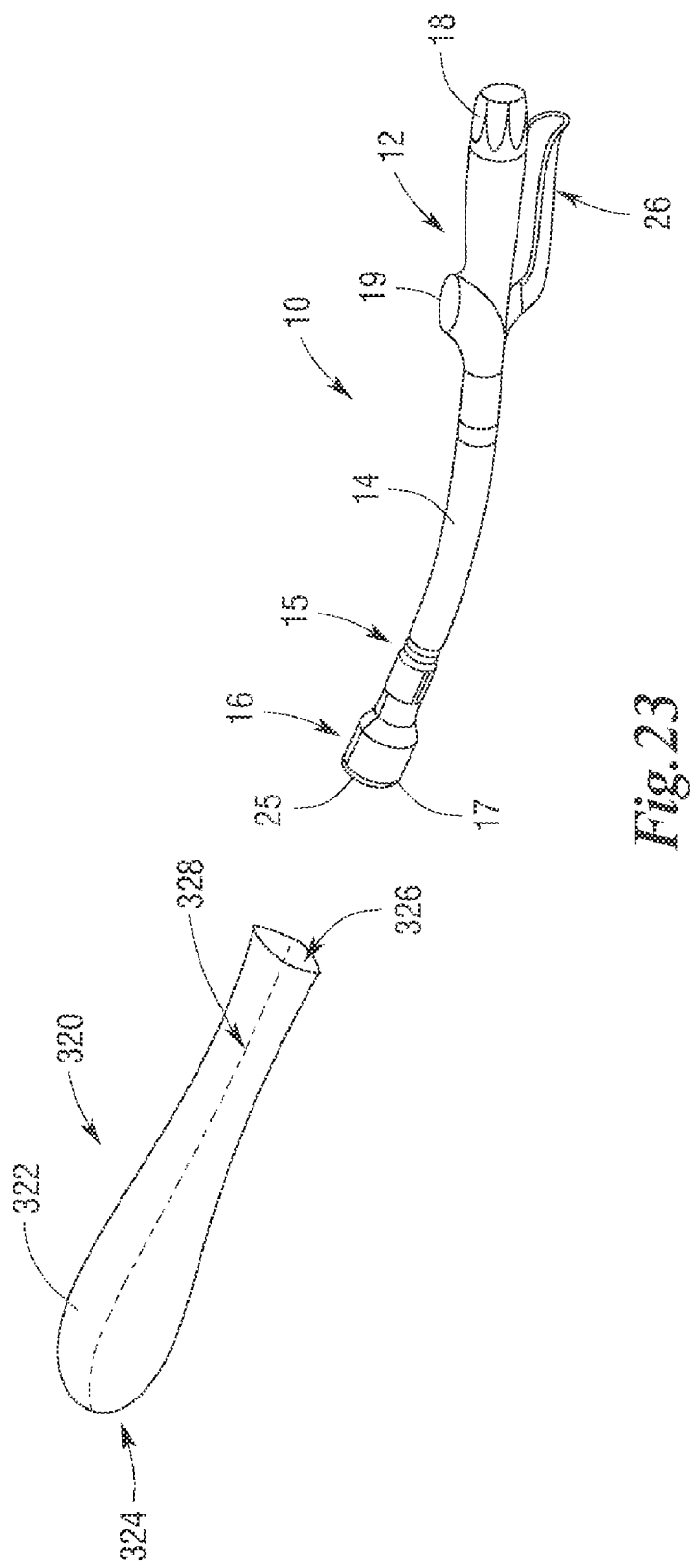
FIG. 23 is a perspective view of a circular surgical stapling instrument prior to the installation of another introducer embodiment of the present invention thereon.

FIG. 23 illustrates another introducer 320 of the present invention. In this embodiment, the introducer 320 comprises a hollow sheath 322 that has a closed end 324 and an open end 326 for insertion onto the circular stapler 10. The sheath 322 may be fabricated from a flexible material such as that material commonly employed to fabricate condoms. In one embodiment, the sheath 320 has a closed end 342 and an open end 326 and is provided with at least one weakened area 328 which may comprise a perforated line or seam that extends the length of the sheath 322. Thus, the sheath 322 is inserted over the stapling head 16 of the stapler 10 prior to insertion into the patient. After the stapler 10 has been inserted into position, the sheath 322 may be removed by pulling on the weakened area 328 to permit the sheath 322 to be separated from the stapler 12.

Figure 24:
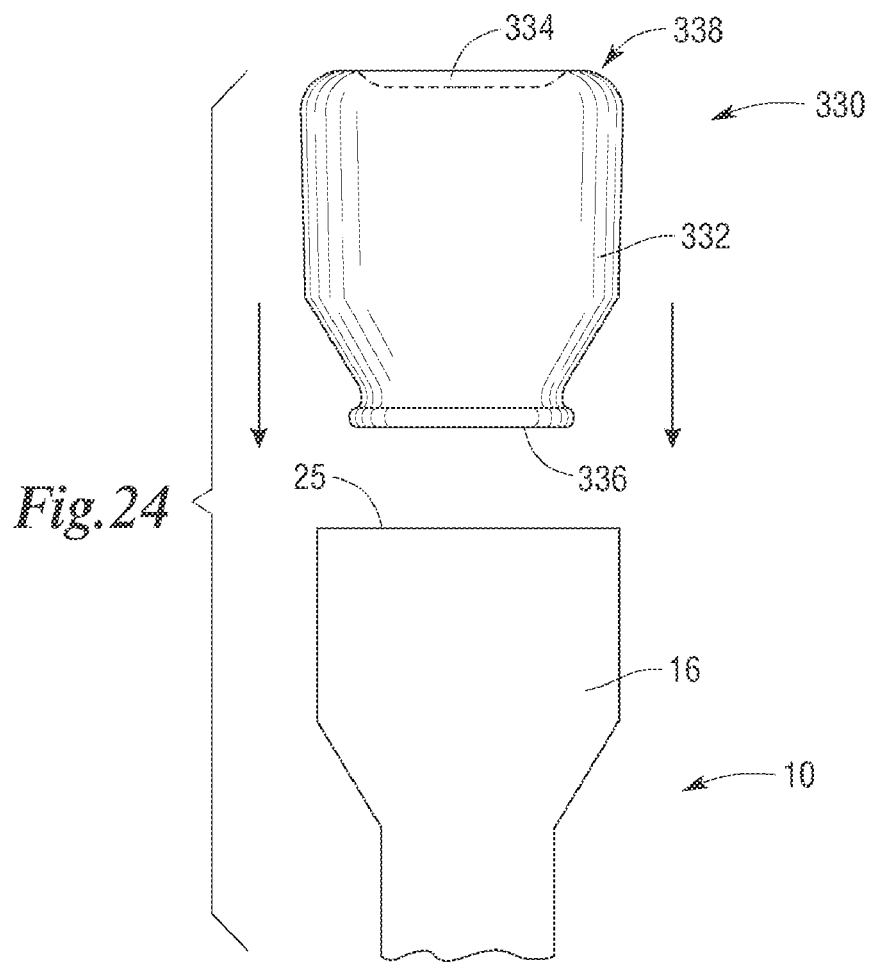
FIG. 24 is an exploded elevational view illustrating another introducer embodiment of the present invention prior to installation on a portion of a stapling head of a circular stapler.
Figure 25:
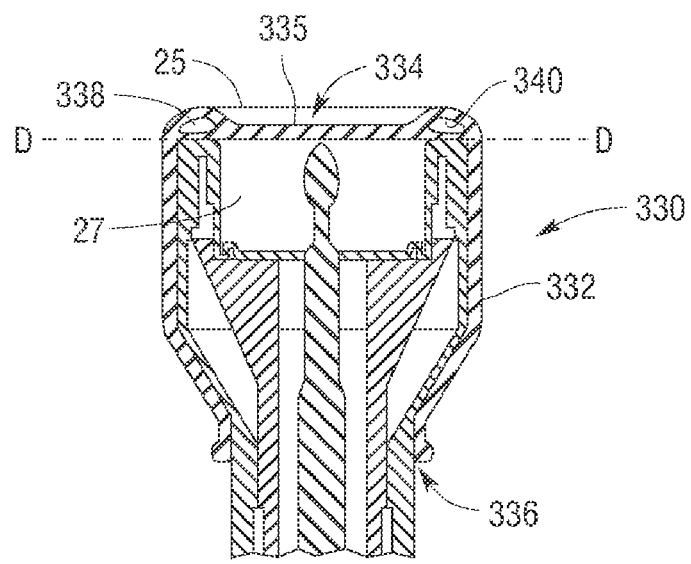
FIG. 25 is a cross-sectional view of the introducer of FIG. 24 installed on a stapling head of a circular stapler.
Figure 27:
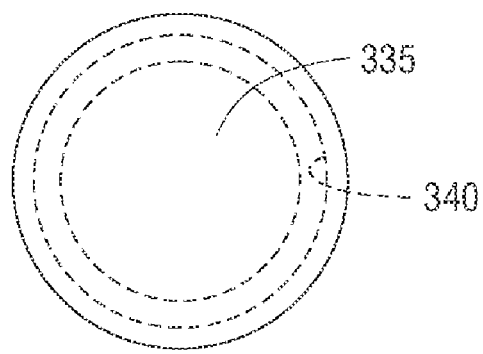
FIG. 27 is a distal end view of another introducer embodiment of the present invention.
Figure 26:
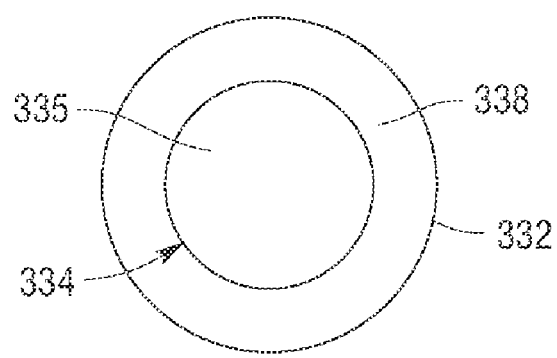
FIG. 26 is a distal end view of an introducer embodiment of the present invention.
Figure 28:
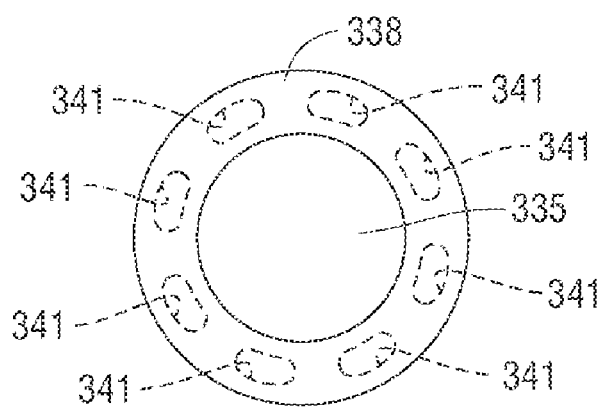
FIG. 28 is a distal end view of another introducer embodiment of the present invention.

FIGS. 24-28 illustrate another introducer 330 of the present invention. In this embodiment, the introducer 330 comprises a sheath 332 that has a closed distal end 334 and an open proximal end 336 that is sized to be stretched over at least a distal portion of the stapling head 16 of the circular stapler 10. The sheath 332 may be fabricated from, for example, silicone, latex or other relatively low durometer material (i.e., a durometer of 90 A). In various embodiments, a circumferentially-extending raised bumper area 338 may be formed around the circumference of the closed distal end 334 as shown in FIGS. 24 and 25. In some embodiments, a central portion 335 extends inwardly from the circumferentially-extending bumper area 338 to enclose an open central area 27 in the stapling head 16. See FIG. 25.

As can also be seen in FIG. 25, the bumper area 338 extends distally beyond (or in other words is "raised above") a plane D-D defined by a distal face 25 of the stapling head 16. In some embodiments, the bumper area 338 is formed from solid material. See FIG. 26. In other embodiments, a circumferentially-extending hollow area 340 is formed therein. In other embodiments, hollow area 340 comprises a plurality of pockets 341. See FIG. 28. The area 340 and pockets 341 may be filled with air or a liquid such as saline solution for example. In use, the sheath 332 is rolled over the stapling head 16 of the stapler 10. The sheath 332 may be left in place while closing and firing the stapler 10 in which case the area 340 or pockets 341 would be broken leaving only the sheath material behind under the staple crown inside the rectal lumen.

Figure 29:
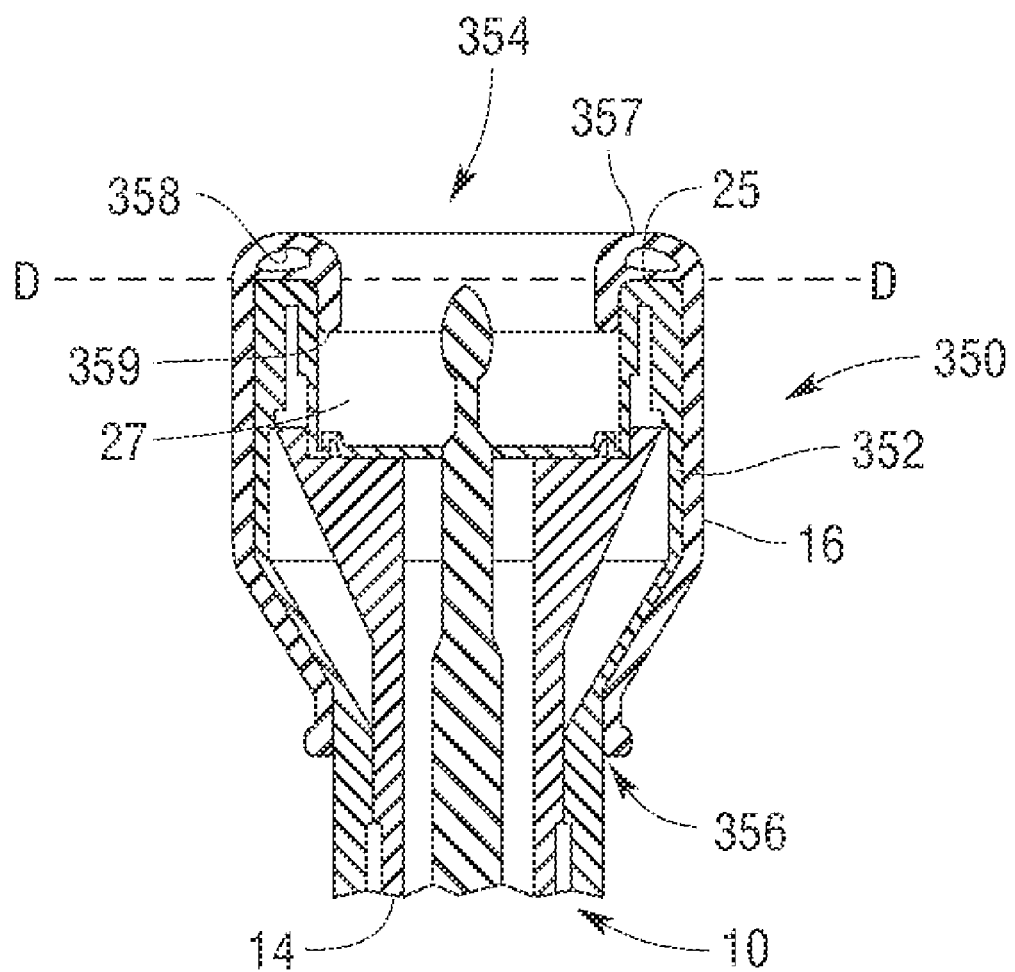
FIG. 29 is a cross-sectional view of another introducer embodiment of the present invention installed on a stapling head of a circular stapler.

FIG. 29 illustrates another introducer 350 of the present invention. In this embodiment, the introducer 350 comprises a sheath 352 that has a distal end 354 and an open proximal end 356 that is sized to be stretched over the stapling head 16 of the circular stapler 10. The sheath 352 may be fabricated from, for example, silicone, latex or other relatively low durometer material (i.e., a durometer of 90 A). In various embodiments, a circumferentially-extending raised bumper area 357 may be formed around the circumference of the sheath 352 such that it covers the distal face 25 of the stapling head 16 and a portion 359 extends into the central open area 27 and below the plane D-D defined by the distal face 25. See FIG. 29. In some embodiments, the bumper area 357 is formed from solid material. In other embodiments, a circumferentially-extending hollow area 358 is formed therein. The hollow area 358 may be filled with air or a liquid such as saline solution. In other embodiments, the circumferentially extending hollow area 358 is segmented (e.g., comprises a series of discrete pockets that extend around the circumference of the sheath 352). The discrete pockets may be filled with air or liquid such as saline solution for example. In use, the sheath 352 is rolled over the distal end portion of the stapling head 16. The sheath 352 may be left in place while closing and firing the stapler 10 in which case the hollow area 358 or pockets would be broken leaving only the sheath material behind under the staple crown inside the rectal lumen.

FIGS. 30-32 illustrate another introducer 360 of the present invention. In this embodiment, the introducer 350 comprises a cover 362 that is sized to be installed on at least a distal portion of the stapling head 16. In one embodiment, the cover 362 comprises a "C"-shaped body portion 363 that may be fabricated from, for example, polyurethane blends, polyesters, polyethylene, polycarbonate or polypropylene and be sized to be snapped onto the stapling head 16 and portion of the elongated shaft 14 of the circular stapler 10. See FIG. 31. In various embodiments, the distal end 364 of the body portion 363 has at least three normally closed fingers 366 that, when moved distally on the stapling head 16, close together forming, for example, a "tulip-like" shape for insertion into the anus. See FIG. 30. The body portion 363 may have a retraction member 370 formed thereon for facilitating the application of a retraction motion thereto. When the stapler 10 has reached its targeted insertion point, the cover 362 may be pulled toward the handle portion 12 of the stapler 10, thus pulling the fingers 366 to the vertical sides of the stapling head 16 exposing the distal face 25 of the staple cartridge 17. See FIG. 32.

Figure 33:
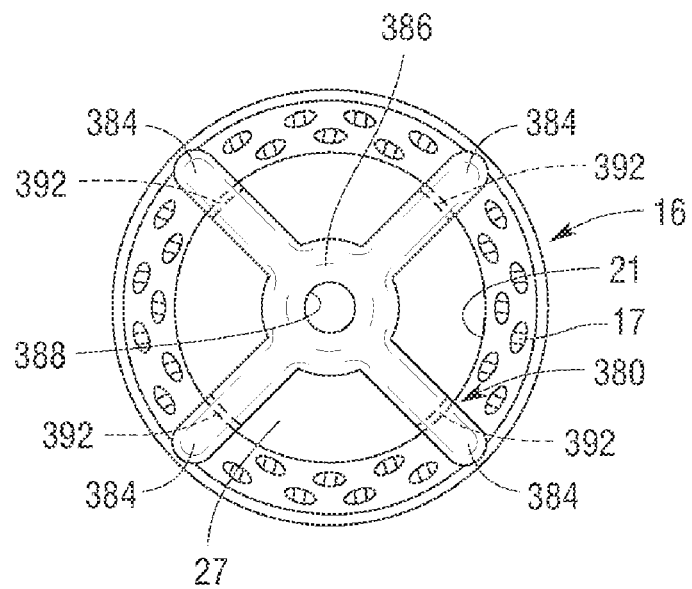
FIG. 33 is a distal end view of another introducer embodiment of the present invention attached to the stapling head of a circular stapler.
Figure 34:
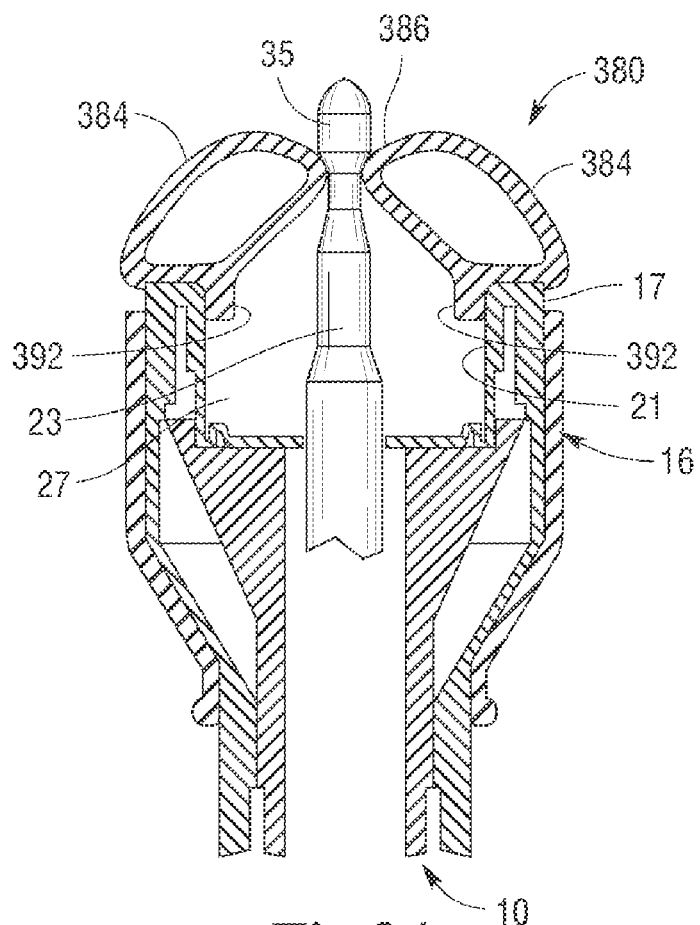
FIG. 34 is a side elevational view of another introducer embodiment of the present invention attached to the stapling head of a circular stapler with the trocar portion of the circular stapler in an extended position.

FIGS. 33 and 34 illustrate another introducer 380 of the present invention. In this embodiment, the introducer 380 comprises a cover 382 that includes four fingers 384 that extend from a centrally disposed hub 386 that has a trocar access hole 388 therethrough. The proximal end 390 of each of the fingers 384 has a retention flange 392 formed thereon that extend into the central opening 27 and engage the central wall portion 21 of the stapling head 16. To install the cover 382, the cover 382 is positioned over the stapling head 16 as shown in FIGS. 33 and 34 and the trocar 23 of the circular stapler 10 is advanced such that the distal end portion 35 of the trocar 23 protrudes through the hole 388 in the central hub 386. Once in position, the trocar 23 is retracted proximally into central opening 27 to thereby force the fingers 384 into a generally bulbous, "mushroom-like" cross-sectional shape. Once the stapler 10 is positioned in the rectum, the trocar 23 can then be deployed and pushed thru the rectal wall allowing access to the accessory fingers 384 which can be removed from the trocar 23.

Figure 35:
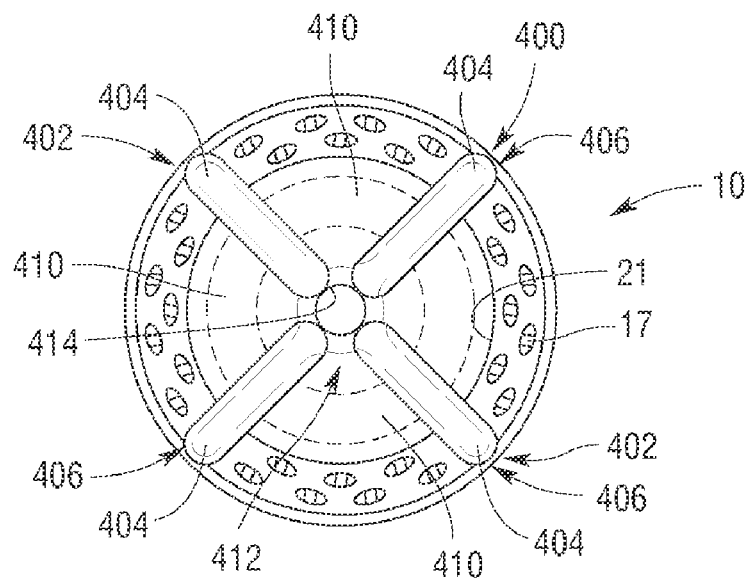
FIG. 35 is a distal end view of another introducer embodiment of the present invention attached to the stapling head of a circular stapler.
Figure 36:
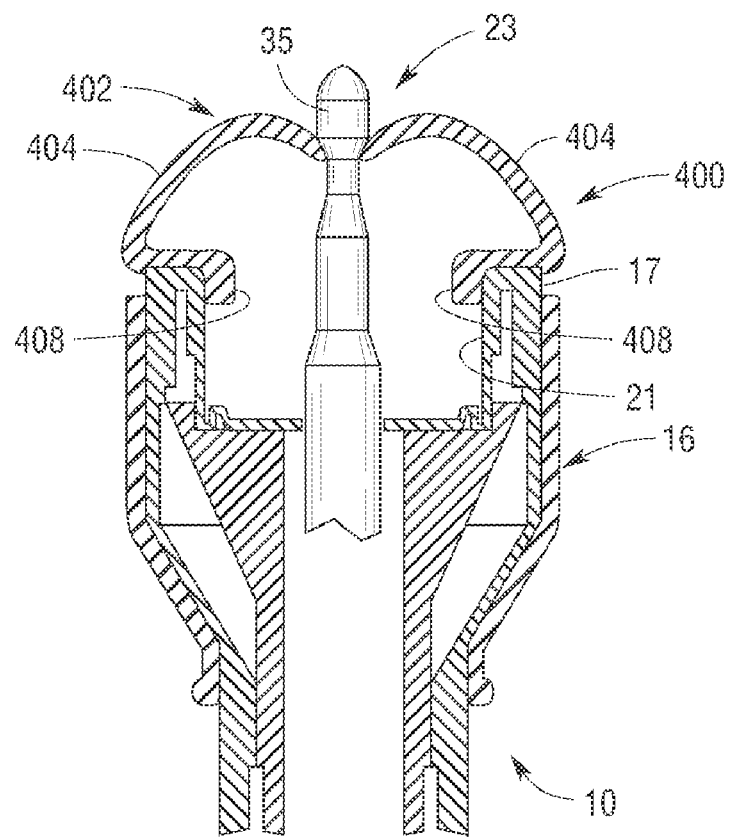
FIG. 36 is a side elevational view of another introducer embodiment of the present invention attached to the stapling head of a circular stapler with the trocar portion of the circular stapler in an extended position.
Figure 37:
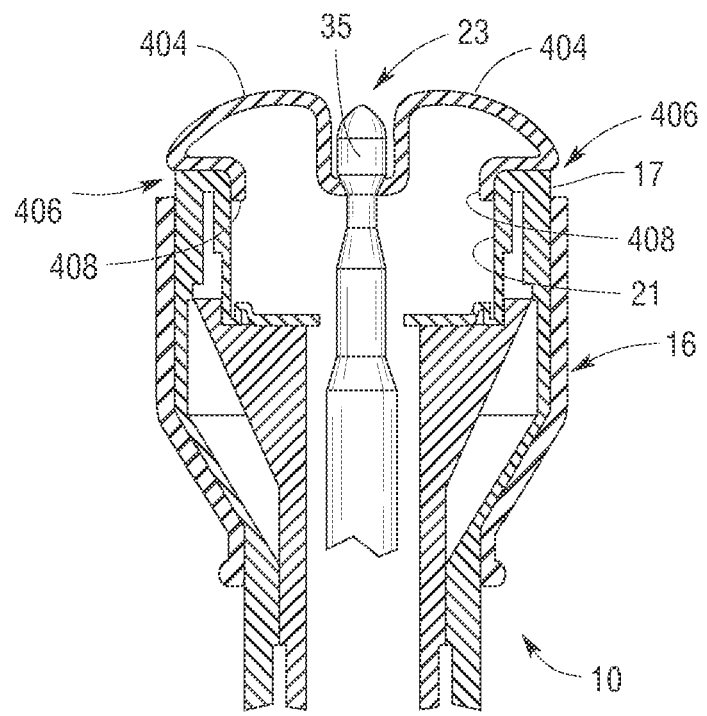
FIG. 37 is another side elevational view of the introducer and stapling head of FIG. 36 with the trocar portion of the circular stapler in a withdrawn position.

FIGS. 35-37 illustrate another introducer 400 of the present invention. In this embodiment, the introducer 400 comprises a cover 402 that include four fingers 404 that are attached together by a sheath 410. See FIG. 35. The sheath may be made from, for example, silicone material. The apex area 412 of the sheath 410 may have a trocar access hole 414 therethrough. The proximal end 406 of each of the fingers 404 has a retention flange 408 formed thereon that extend into the central opening 21 in the stapling head 16. To install the cover 400, the cover 402 is positioned over the stapling head 16 as shown in FIGS. 35 and 36 and the trocar 23 of the circular stapler 10 is advanced distally such that the distal end portion 35 of the trocar 23 protrudes through the hole 414 in the sheath 410. Once in position, the trocar 23 is retracted to thereby force the fingers 404 into a generally mushroom cross-sectional shape. See FIG. 37. Once the stapler 10 is positioned in the rectum, the trocar 23 can then be deployed and pushed thru the rectal wall allowing access to the accessory fingers 404 which can be removed from the trocar 23.

Figure 38:
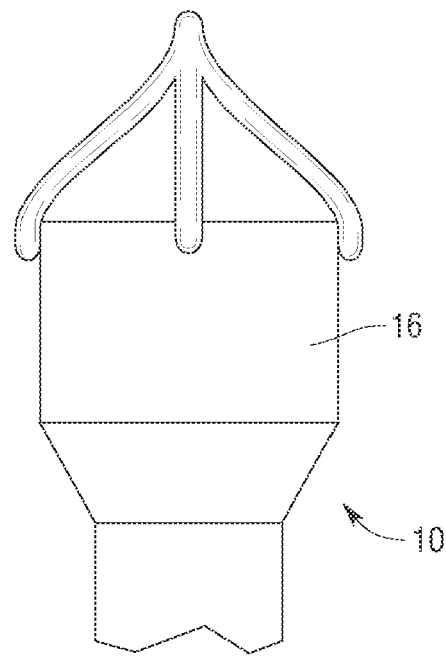
FIG. 38 is a side elevational view of another introducer embodiment of the present invention attached to a stapling head of a circular stapler.

FIG. 38 illustrates another introducer 420 that may be fabricated from, for example, polyurethane blends, polyesters, polyethylene, polycarbonate or poly propylene that has at least four fingers 422 that are interconnected at a hub or apex area 424. The proximal ends 426 of the fingers 422 snap onto the stapling head 16. In this embodiment, the introducer 420 is designed to go up the colon and then be removed. This is unlike the introducer 400 described above wherein the trocar is in the extended position to hold it in place until the device is in position and then the trocar is brought proximally.

FIGS. 39 and 40 illustrate another introducer 500 that may be used in connection with a circular stapler 10. As can be seen in those Figures, the introducer 500 may comprise a molded arrangement with perforations and may be fabricated from, for example, polyurethane blends, polyesters, polyethylene or polypropylene or alternatively could comprise wound strip that is sewn together or held in place without covering. The strip 504 may have a width of, for example, 0.250 inches and a thickness of, for example, 0.020 inches. The strip 504 may form a base portion 506 sized to extend around the circumference of the stapling head 16. The base portion 506 may be sized relative to the stapling head 16 such that, when held together in close spiral relationship, the spiral strip 504 forms a relatively tight (interference) fit with the stapling head 16 to retain the introducer thereon. The spirally wound strip 504 forms a plurality of successive passes 508 that tapers to a blunt distal end 510. As can be seen in FIG. 36, one embodiment resembles a blunt-ended "beehive-shape" that substantially encloses or covers the distal face of the stapling head 16. The spiral passes 508 may be held in substantial abutting relationship (i.e., spirally wound closed ended relationship) by a retainer member 510. In various embodiments, the retainer member 510 may comprise a thin (e.g., 1 to 4 Mils) layer of shrink wrap that extends over the introducer 500. The introducer 500 also includes a release member 520 that is attached to the strip material 504 such that upon application of a release motion thereto, the spiral wound strip member 504 is unwound from engagement with the distal portion of the stapling head 16. In one embodiment, for example, the release member comprises a release suture 520 that is attached to the distal end 512 of the strip 504. The release suture 520 may pass through a hole 522 in a portion of the strip 504 forming the base portion 506 and extend proximally out to the handle portion of the stapler 10 to enable the release suture 520 to be grasped by the clinician.

The introducer 500 may be installed by the supplier of the stapler 10 by shrink wrapping the introducer 500 to the stapling head 16. In use, the clinician inserts the stapler and introducer assembly 530 into the patient's anus and past the Valves of Houston to the desired area. Once the clinician has determined that the stapler 10 is in the desired position, the clinician can then pull the release suture 520 in the proximal direction "P" which causes the shrink wrap 510 to rupture thereby permitting the introducer 500 to unwind as illustrated in FIG. 40. Continued pulling on the release suture 520 will enable the introducer 500 to be withdrawn from the patient.

FIGS. 41-43 illustrate another introducer 600 that may be used in connection with a circular stapler 10. As can be seen in those Figures, the introducer 600 may have a base portion 602 sized to be retained on the stapling head 16. The introducer 600 is formed with a plurality of tapered "petal" portions 504 that taper to a substantially rounded point 606. In some embodiments, for example, there are four diametrically opposed petal portions 604 that, when closed (FIG. 41), converge to form a relatively blunted pointed end 610. The petal portions 604 have an open area 612 therebetween. In various embodiments, the petal portions 604 are retained in the closed position by a releaseable retainer member 620. In some embodiments for example, the retainer member comprises shrink-wrap material 620 that is applied around the introducer 600. In some embodiments, a plurality of retention ledges 630 may be formed around the inner perimeter of the base 602 to engage the distal face 25 of the stapling head 16 when the shrink wrap 620 has been applied. Release sutures 640 may be sewed through those portions 622 of the shrink-wrap 620 that cover the open area 612. The release sutures 640 terminate in or are each attached to a release suture 650 that passes through a hole 652 in the base portion 602 and extends proximally out to the handle portion of the stapler 10 to enable the release suture 650 to be grasped by the clinician.

The introducer 600 may be installed by the supplier of the stapler 10 by shrink wrapping the introducer 600 to the stapling head 16. In use, the clinician inserts the stapler and introducer assembly 660 into the patient's anus and past the Valves of Houston to the desired area. Once the clinician has determined that the stapling head of the stapler 10 is in the desired position, the clinician can then pull the release suture 650 in the proximal direction "P" which causes the shrink-wrap 620 to rupture thereby permitting the introducer 600 to be pulled distally over the stapling head 16 as illustrated in FIG. 43.

FIGS. 44-46 illustrate another introducer 700 that may be used in connection with a circular stapler 10. As can be seen in those Figures, the introducer 700 may be fabricated from, for example, polyurethane blends, polyesters, polyethylene or polypropylene and have a base portion 702 sized to be retained on the stapling head 16. The introducer 700 is formed with a plurality of tapered "segment" portions 704 that taper to a substantially rounded point 706. In some embodiments, for example, there are four diametrically opposed segment portions 604 that, when closed (FIG. 44), converge to form a relatively blunted pointed end 710. In the embodiment depicted in FIGS. 44-46, the introducer 700 includes four segment portions 704. The segment portions 704 are interconnected at their base portions except for two adjacent segment portions 704 wherein the bases of the two segment portions 704 are not attached together. More particularly, segment portion 704A has a base edge 705A and segment portion 704B has a base edge 705B. Edges 705A and 705B are not attached to each other. Thus, segment portion 704A and segment portion 704B comprise free ends of the base portion 702. The free ends 704A and 704B are retained in abutting relationship by a retainer member in the form of a radial release tab 720 that is attached to 704A and 704B. In various embodiments, the release tab 720 is fixed or molded to segment portion 704A and may not necessarily be removed therefrom. The release tab 720 is releaseably attached to segment portion 704B. The release tab 720 may be attached to the segment portion 704 by a releasable retainer 722 such as, for example, a releasable adhesive or piece of rupturable material. When the release tab 720 is attached as shown in FIG. 41, the segment portions 704 form an annular base portion 702 that may be retainingly snapped onto or otherwise retainingly engage the stapling head 16 of the circular stapler 10. A release suture 730 is attached to the release tab 720 and extends proximally out to the handle portion 12 of the stapler 10 to enable the release suture 730 to be grasped by the clinician.

The introducer 700 may be snapped onto or pressed onto the stapling head 16 by the clinician. In use, the clinician inserts the stapler and introducer assembly 740 into the patient's anus and past the Valves of Houston to the desired area. Once the clinician has determined that the stapling head 16 of the stapler 10 is in the desired position, the clinician can then pull the release suture 730 in the proximal direction "P" which causes the release tab 720 to release from the segment portion 704B to enable the introducer 700 to release from the stapling head 16. Continued pulling on the release suture 730 will enable the introducer 700 to be withdrawn from the patient.

Thus, the various embodiments of the circular stapler introducer of the present invention may facilitate the transanal and transabdominal insertion and navigation to access the staple line of the distal stump in lower anterior resections. The various introducers may be provided as a part of a kit that also includes a circular stapler 10. Various embodiments of the introducer will have no impact on the current functions of the circular stapler.

The various embodiments of the present invention represent a vast improvement over prior circular staple arrangements that fail to provide any means for locking the anvil in a firing position. While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. An introducer for introducing a surgical circular stapler into a patient, the circular stapler having a handle portion, an elongated shaft protruding from the handle portion, and a stapling head coupled to the elongated shaft, said introducer comprising:
   a hollow flexible sheath having a distal end and an open proximal end, said hollow flexible sheath sized to receive the stapling head and at least a portion of the elongated shaft therein; and
   a rigid cap assembly attached to said distal end of said hollow flexible sheath, said rigid cap assembly configured to selectively move between a closed position wherein a distal face of the stapling head is covered by said rigid cap assembly when the stapling head has been inserted therein to a fully inserted position and an open position wherein said cap assembly may be proximally withdrawn from around the stapling head and elongated shaft, said cap assembly having a portion shaped to match a shape of a perimeter of a corresponding portion of the stapling head to enable the rigid cap assembly to pass proximally past the stapling head when being withdrawn therefrom.

2. The introducer of claim 1 further comprising a release arrangement interfacing with said rigid cap assembly to releaseably retain said rigid cap assembly in said closed position.

3. The introducer of claim 1 wherein said rigid cap assembly comprises:
   a barrel member coupled to said distal end of said hollow flexible shaft and defining an opening sized to receive the stapling head therethrough; and
   a rigid cap member hingably attached to said barrel member and being movable between said closed position and said open position.

4. The introducer of claim 3 wherein said rigid cap member has a substantially smooth distal surface.

5. The introducer of claim 3 wherein said portion shaped to match a shape of a perimeter of a corresponding portion of the stapling head comprises an underside of said rigid cap member.

6. The introducer of claim 5 wherein the stapling head has a circular perimetrical shape and wherein said underside of said rigid cap member has an arcuate shape that substantially matches a portion of said circular perimetrical shape of the stapling head.

7. The introducer of claim 3 further comprising a release arrangement interfacing with said barrel member such that upon an application of a release motion thereto, said rigid cap member is movable to said open position.

8. The introducer of claim 7 wherein said release arrangement comprises a release latch in movable engagement with latch portions on said barrel member.

9. The introducer of claim 8 wherein said cap member is hingably attached to said barrel member by a tether attached to said barrel member in a position that is substantially diametrically opposite from said latch portions on said barrel member.

10. The introducer of claim 8 wherein said cap member is hingably attached to said barrel member by a tether attached to said barrel member in a position that is located at a substantial right angle from said latch portions on said barrel member.

11. The introducer of claim 3 wherein said cap member has a cross-sectional area that is larger than a cross-sectional area of the barrel member.

12. The introducer of claim 3 wherein said cap member is more rigid than said barrel member.

13. The introducer of claim 6 further comprising a plurality of ribs formed in said underside of said cap member.

14. An introducer for introducing a surgical circular stapler into a patient, the circular stapler having a handle portion, an elongated shaft protruding from the handle portion, and a stapling head coupled to the elongated shaft, said introducer comprising:
   a hollow flexible sheath having a distal end and an open proximal end, said hollow flexible sheath sized to receive the stapling head and at least a portion of the elongated shaft therein;
   a radially-openable barrel member attached to a distal end of said hollow flexible sheath and defining an opening for receiving the stapling head therein,
   a latch member in engagement with a pair of opposed ends of said radially-openable barrel member, said latch member being selectively movable from a latched position engaging said opposed ends of said barrel member and an unlatched position wherein said opposed ends may move radially away from each other; and
   a rigid cap member hingably attached to said radially-openable barrel member and being movable between a closed position wherein said rigid cap member is retained in a closed position covering a distal end of said opening in said barrel member and an open position wherein said rigid cap member is movable to a position exposing said distal end of said opening in said barrel member, said rigid cap member having an underside with a shape that matches a shape of a perimeter of a corresponding portion of the stapling head to enable said rigid cap member to pass proximally past the stapling head when being proximally withdrawn therefrom.

15. The introducer of claim 14 wherein the stapling head has a circular perimetrical shape and wherein said underside of said cap member has an arcuate shape that substantially matches a portion of said circular perimetrical shape of the stapling head.

16. The introducer of claim 14 wherein said cap member is hingably attached to said barrel member by a tether attached to said barrel member in a position that is substantially diametrically opposite from said latch member.

17. The introducer of claim 14 wherein said cap member is hingably attached to said barrel member by a tether attached to said barrel member in a position that is located a substantial right angle from said latch member.

18. The introducer of claim 15 wherein said cap member has a blunt distal end surface that is substantially smooth.

19. An introducer for introducing a surgical circular stapler into a patient, the circular stapler having a handle portion, an elongated shaft protruding from the handle portion, and a stapling head coupled to the elongated shaft, said introducer comprising:
   flexible means for removably encasing the stapling head and at least a portion of the elongated shaft of the circular stapler; and
   end means for selectively presenting a rigid blunt surface covering a distal face of the stapling head, said end means on a distal end of said means for removably encasing, and said end means comprising:
   means for selectively exposing the distal face of the stapling head; and
   means for presenting a surface configured to match a portion of a perimetrical shape of the stapling head when in an open position to enable the end means to pass proximally past the stapling head when being proximally withdrawn therefrom.

20. The introducer of claim 19 wherein said flexible means comprises an open-ended sheath extending from said end means to the handle portion of the circular stapler when the stapling head and elongated shaft portion are fully inserted therein.

* * * * *